United States Patent
Metcalf et al.

(10) Patent No.: US 6,613,317 B1
(45) Date of Patent: Sep. 2, 2003

(54) VOLATILE ATTRACTANTS FOR DIABROTICA SPECIES

(75) Inventors: Robert L. Metcalf, Urbana, IL (US); Richard L. Lampman, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 07/882,351

(22) Filed: May 6, 1992

Related U.S. Application Data

(63) Continuation of application No. 07/759,114, filed on Sep. 6, 1991, now abandoned, which is a continuation of application No. 07/453,950, filed on Nov. 13, 1989, now abandoned, which is a continuation-in-part of application No. 07/170,159, filed on Mar. 18, 1988, now Pat. No. 4,880,624.

(51) Int. Cl.$^7$ .............................................. A01N 25/00
(52) U.S. Cl. ........................................................ 424/84
(58) Field of Search ........................................... 424/84

(56) References Cited

FOREIGN PATENT DOCUMENTS

CA          1195922          10/1985  .................. 167/5.3

OTHER PUBLICATIONS

Andersen, J. Agric. Food Chem., 35:60–62 (1987).
Berry et al, J. Agric. Food Chem., 26:354–356 (1978).
Buttery et al, J. Agric. Food Chem., 26:866–869 (1978).
Buttery et al, J. Agric Food Chem., 28:771–774 (1980).
Buttery et al, J. Agric. Food Chem., 32:1104–1106 (1984).
Chambliss et al, Science, 153:1392–1393 (1966).
Chio et al, J. Econ. Entomol., 71:389–393 (1978).
Ferguson et al, J. Econ. Entomol., 76:47–51 (1983).
Howe et al, Environ. Entomol., 5:747–751 (1976).
Howe et al, Environ. Entomol., 5:1043–1048 (1976).
Itokawa et al, Phytochemistry, 21:1935–1937 (1982).
Ladd et al, J. Econ. Entomol., 76:1049–1051 (1983).
Ladd et al, J. Econ. Entomol., 77:339–341 (1984).
Ladd et al, J. Econ. Entomol., 77:652 (1984).
Ladd et al, J. Econ. Entomol., 78:844–847 (1985).
Lampman et al, J. Chem. Ecol., 13:959–975 (1987).
Lampman et al, J. Econ. Entomol., 80:1137–1142 (1987).
Lampman et al, Environ. Entomol., 17:644–648 (1988).
McAuslane et al, Proc. Entomol. Soc. Ontario, 117:49–57 (1986).
Metcalf et al, Cucurbit Genet. Coop. Rept., 4:37–38 (1981).
Metcalf et al, Environ. Entomol., 11:931–937 (1982).
Metcalf, Ill. Nat. Hist. Surv. Bulletin, 33:175–198 (1985).
Metcalf, J. Chem. Ecol., 12:1109–1124 (1985).
Metcalf et al, J. Econ. Entomol., 80:870 (1987).
Metcalf et al, paper submitted to J. Econ. Entomol. (1988).
Metcalf et al, Proc. Nat'l. Acad. Sci. USA, 77:3769–3772 (1980).
Mitchell et al, Environ. Entomol., 14:176–181 (1985).
Morgan et al, J. Econ. Entomol., 21:913 (1928).
Yaro et al, Environ. Entomol., 16:126–128 (1987).
Rhodes et al, J. Am. Soc. Hortic. Sci., 105:838–842 (1980).
Metcalf et al, Cucurbit Genet. Coop Rept., 6:79–81 (1983).

*Primary Examiner*—Russell Travers
(74) *Attorney, Agent, or Firm*—Marshall, Gerstein & Borun

(57) ABSTRACT

Disclosed are attractants and lures for attracting and controlling the adult form of Diabrotica species, in particular northern corn rootworm, useful individually or in mixtures and in combination with insecticides and compulsive feeding stimulants, such as cucurbitacins.

3 Claims, No Drawings

VOLATILE ATTRACTANTS FOR DIABROTICA SPECIES

CROSS-REFERENCE TO RELATED APPLICATION

This application is a continuation of U.S. Ser. No. 07/759,114; filed Sep. 6, 1991; now abandoned which in turn is a continuation of U.S. Ser. No. 07/435,950; filed Nov. 13, 1989; now abandoned which in turn; and is a continuation-in-part of U.S. patent application Ser. No. 07/170,159, filed Mar. 18, 1988 which issued as U.S. Pat. No. 4,880,624 on Nov. 14, 1989.

BACKGROUND OF THE INVENTION

The present invention relates generally to lures for attracting and controlling Diabrotica species. In particular, the invention relates to lures comprising one or more compounds found in the volatile fraction of Cucurbita blossoms, or analogs thereof, alone or in combination with other lures, insecticides, and/or compulsive feeding stimulants.

The chrysomelid genera Diabrotica and Acalymma contain numerous pest species, including the western corn rootworm (WCR), *Diabrotica virgifera virgifera* LeConte; the southern corn rootworm (SCR) or, the spotted cucumber beetle, *D. undecimpunctata howardi* [*D. duodecimpunctate* Fab.]; the northern corn rootworm (NCR), *D. barberi* Smith and Lawerence; and the striped cucumber beetle (SCB), *Acalymma vittatum* (Fabr.).

The western, norther, and southern corn rootworms are the most expensive insect pests of North America and annually cost U.S. farmers approximately one billion dollars in costs associated with lost crop yield and with preventative treatments with soil insecticides. The era of relatively inexpensive crop protection against these pests has ended because of generalized rootworm resistance to organochlorine insecticides and the withdrawal by the U.S. EPA of registrations for these insecticides due to widespread environmental contamination. The newer organophosphorous and carbamate insecticides are more expensive and subject to accelerated microbial degradation in soils and a rapid loss of activity. Furthermore, due to the persistence of many of these soil insecticides, groundwater and surface run-off pollution is of much concern to state and federal agencies. Because of the uncertain performance and safety of the major products currently used for larval rootworm control, such as carbofuran (Furadan™), isofenphos (Amaze™), phorate (Thimet™), terbufos (Counter™), a technological void exists for controlling these pests. Even standard cultural methods of pest management such as crop rotations of corn-soybean-corn and corn are endangered as evidence exists that the northern corn rootworm can undergo an extended diapause for two seasons. Hence, the benefits of yearly crop rotation are threatened.

Present soil insecticide technology for corn rootworm control is rapidly becoming unworkable. The use of volatile attractants, singularly and in combinations with other control methods, can become the basis for a new integrated pest management IPM) technology for rootworm control that is economically favorable for the farmer and certainly much less environmentally objectionable. In this regard, Diabrotica and Acalymma are known to show a close association with host plants of the family Cucurbitaceae, particularly with the genus Cucurbita. Adult beetles are most commonly found in the blossoms of Cucurbita species where they feed on pollen (in staminate flowers) and on nectar. In most instances, adult beetles showed a preference for the blossoms of *C. maxima* Duchesne cultivars over those of *C. pepo* L. and *C. moschata* Poir.

The blossom characteristics, i.e., color, size, shape, and/or fragrance, responsible for this preference are not fully understood, although Diabrotica attraction to certain compounds, termed semiochemicals, has been reported. By way of background, semiochemicals are plant-produced compounds which act by diffusion through air to produce behaviorial responses in associated insect species. Kairomones are those semiochemicals which act to benefit the receiving species; allomones are those which benefit the sending species; and synomones, e.g., floral volatiles involved in pollination, benefit both the emitting plant, through pollination, and the perceiving insect by rewards of nectar and pollen or through more intangible ecological rewards of aggregation or lek formations which lead to mating.

One of the earlier reports relating to Diabrotica attraction to compounds appeared in Morgan, et al., *J. Econ. Entomol.*, 21:913 (1928). This collection of preliminary results on the chemotropic response of certain insects included the observation that the spotted cucumber beetle, *D. undecimpunctata howardi* (as *D. duodecimpuntata* Fab.), was attracted to cinnamaldehyde and cinnamyl alcohol. These results were obtained using white granite-ware pans of about 2-quart capacity set in rows on stakes 2 feet high, and filled with 1 quart of water to which was added 1 cc. of the chemical to be tested. The areas in which experiments were conducted included a field white with the blossoms of the field daisy (*Erigeron annuus*) oatfields, margins of woods, hedge rose, a cane brake, a slaughter-house lot; and a livery-stable yard. There is no indication in the reference as to the degree to which, or the conditions under which, cinnamic aldehyde and cinnamic alcohol acted as attractants. Shapp, et al., *J. Econ. Entomol.*, 22:98 (1929) disclosed a preliminary report indicating that the spotted cucumber beetle was attracted by oil of thyme (white) and benzyl alcohol. However, in tests by Lampman, et al, *J. Chem. Ecol.*, 13:959 (1987) benzyl alcohol was shown to have negligible attractant value.

Ladd, et al., *J. Econ. Entomol.*, 76:1049 (1983), studying a mixture of phenethyl proprionate, eugenol, geraniol, a food-type lure for Japanese beetles, reported that eugenol was attractive to adults of *D. barberi* Smith & Lawrence (NCR), but not attractive to *D. virgifera virgifera* LeConte (WCR). Ladd, T. L., *J. Econ. Entomol.*, 77:339 (1984) tested nine compounds closely related to eugenol for attractancy to NCR including four groups: eugenol and its close relatives with isomeric or saturated hydrocarbon side chains; eugenol acetate and its isomer; anethole and its analogs with isomeric or saturated side chains; and a miscellaneous group consisting or methyleugenol and 2-allyl-6-methoxyphenol (orthoeugenol). The author reported two new attractants for NCR, isoeugenol and 2-methoxy-4-propylphenol and concluded that while neither the position of the double bond in the side chain nor the degree of saturation appeared critical in attracting NCR the presence of the methoxy and hydroxyl groups at their respective positions (adjacent), particularly the latter, seemed to be important. Yaro, et al., *Environ. Entomol.*, 16:126 (1987) reported that eugenol and 2-methoxy-4-propyl phenol were highly attractive to *D. cristata* Harris ( a non-pest species) and *D. barberi* Smith & Lawrence, whereas isoeugenol acetate was not attractive. None of the compounds was highly attractive to *D. virgifera vigifera* LeConte. Ladd, et al., *J. Econ. Entomol.*, 77:652 (1984) also conducted tests to study the influence of color and height of eugenol-baited sticky traps and reported that the traps were most effective when painted yellow and placed 0 to 0.25 m above ground.

Another recent report of investigations concerning a chemical basis for Diabrotica orientation to the blossoms or foilage of Cucurbita species was in Andersen, et al., *J. Chem. Ecol.*, 12:687 (1986). The authors screened *C. maxima* "Blue Hubbard" blossom volatiles for electroantennogram (EAG) activity, a laboratory test for insect electrophysiological response to volatile compounds, and found two fractions had significant activity for the southern corn rootworm. The first peak consisted of indole and the second, smaller peak, was not characterized. Indole was then field tested for insect responsiveness and found to be a potent attractant of the western corn rootworm and of the striped cucumber beetle. However, the southern corn rootworm was not attracted at any dosage level despite the strong EAG response.

Anderson, et al., *J. Chem. Ecol.*, 13:681 (1987) subsequently characterized the blossom constituents of attractive Cucurbita floral volatiles from a number of cultivars representing *C. moschata*, *C. pepo*, and *C. maxima*, and examined other factors, including nutritional and secondary chemical characteristics, that might influence beetle field distribution in blossoms. They found paradimethoxybenzene to be a major constituent of headspace samples from cultivated Cucurbita cultivars. The Diabrotica species showed a clear preference for certain cultivars. SCR preferred the blossoms of *C. maxima* cultivars, while WCR preferred the cultivars of *C. maxima* as well as a single cultivar of *C. pepo*. The authors suggested that NCR and SCR are similar in their most preferences, each strongly favoring *C. maxima*, whereas WCR appeared to find a broader range of cultivars acceptable. No firm conclusions were reached with respect to whether the gustatory cues, i.e., the levels of cucurbitacins, and olfactory cues, i.e., floral odors and level of release, acted individually or in concert, along with visual qualities to produce the patterns of preferences exhibited by the various species of Diabrotica.

Seasonal variations in responses to attractants have also been observed. As noted earlier, Andersen, et al., *J. Chem. Ecol.*, 12:687 (1986) found that indole elicited a strong EAG response from SCR, but was wholly ineffective as an attractant in field tests. However, Lampman, et al., *J. Chem. Ecol.*, 13:959 (1987) subsequently found that indole was in fact a moderately active attractant for SCR late in the season. In that study, the authors field tested various blossom volatiles and related compounds and found that southern, western, and northern corn rootworm adults exhibited not only a species specific response but also a seasonal pattern of response to sticky traps baited with various benzenoid compounds. SCR adults were attracted in early to mid-August to traps baited with veratrole (1,2-dimethoxybenzene), phenylacetaldehyde, and chavicol (4-hydroxy-1-allylbenzene). In late August and September, SCR trap catches dramatically increased for veratrole and phenylacetaldehyde, as well as for some compounds previously unattractive compounds, such as indole, several eugenol-related compounds, benzyl acteone, and phenethyl alcohol. WCR adults were significantly attracted to a different group of compounds, namely estragole, trans-anethole, and indole. Estragole (4-methoxy-1-allylbenze) was an effective WCR attractant from early August until the end of the trapping period in late September and early October. Indole and trans-anethole (4-methoxy-1-propenylbenzene) were less effective attractants than estragole and were most active at the begining and/or end of the corn sesason. The para-methoxy ring substituent and the position of the double bond in the propanoid side chain were noted to be critical for maximum WCR response; compounds differing in either aspect were less attractive. The phenyl propanoids, eugenol and isoeugenol, significantly attracted NCR adults. Ladd, T. L., *J. Econ. Entomol.*, 77:339 (1984) previously found that NCR response is optimal for phenylpropanoids with a meta-methoxy and para-hydroxy substituent. Both Ladd, supra, and Lampman, et al., supra, noted a seasonal variability in response to eugenol and isoeugenol.

A comparison between the rootworm species indicated that the ecologically similar NCR and WCR adults are attracted to structurally related phenylpropanoids and both species respond to changes in the ring substituents of the major attractants. However, WCR and NCR adults are not attracted to the same phenylpropanoids, although SCR adults are occasionally attracted to indole (a WCR attractant) and to eugenol and isoeugenol (NCR attractants). The authors in Lampman, et al., supra, also noted (and subsequently reported in Metcalf, et al., *J. Econ. Entomol.*, 80:870 (1987)) an increase in SCR trap catch for either eugenol or veratrole added to insecticide-impregnated cucurbitacin baits. Apparently, SCR adults cross-responded (especially late in the season) to some WCR and NCR attractants, although the main attractants for each species was highly specific.

The foregoing results suggested that Diabrotica are attracted to certain single component attractants; however, none of these attractants demonstrated the requisite degree of attraction required to effectively control and manage populations of Diabrotica. Thus, there exists a need in the art for an alternative safe and effective method for management of Diabrotica species which is effective in controlling the more visible stage of the insect pests, i.e., the adult, yet which is economical and which abolishes the need for the use of soil insecticides.

BRIEF SUMMARY OF THE INVENTION

The present invention provides novel attractants for the control of Diabrotic species insects, novel mixtures of attractants and novel compositions including, in combination, Dibrotica species attractants, diabroticiticidal insecticides and compounds and compositions functional as compulsive stimulants of Diabroticite feeding behavior.

Novel attractants provided according to the invention include: β-ionone; 4-methoxycinnamaldehyde; 4-methoxycinnamonitrile; 4-methoxy-1-vinyl-benzene; 4-methoxy-1-propyl-benzene; 4-methoxy phenyl ethyl ether; 4-methoxy phenyl acetonitrile; allyl benzene; cinnamonitrile; 2-methoxy cinnamaldehyde; cinnamyl acetate; cinnamic acid methyl ester; dihydrocinnamyl aldehyde; and phenyl propionitrile.

Also provided are the following novel attractants: 4-methylphenylethanol, 4-chlorophenylethanol, 4-fluorophenylethanol, phenylethanol, phenylpropanol, 4-methoxyphenylethanol, 3-methoxyphenlyethanol, 2-methoxyphenylethanol, 4-methoxyphenylpropanol, phenylethylamine, and phenylpropylamine.

These novel attractants are suitable for use individually or in combination with each other or known Diabrotica species attractants.

Novel mixtures of attractants according to the invention are seen to include a compound selected from the group consisting of dimethoxybenzene, trimethoxybenzene, and guaiacol admixed with one or more compounds selected from the group consisting of indole, phenylacetaldehyde, anethole, eugenol, cinnamaldehyde and cinnamonitrile. Presently preferred dimethoxybenzene compounds include orthodimethoxybenzene ("veratrole") as well as the meta- and para-forms. Of the isomeric forms of trimethoxybenzene, the 1,2,4-trimethoxy form is preferred. Presently preferred attractant mixtures include the following: veratrole and indole (VI); veratrole and phenlyacetaldehyde (VP); veratrole, indole and phenylacetaldehyde (VIP); meta-dimethoxybenzene, indole and phenylacetaldehyde (mDMBIP); para-dimethoxybenzene, indole and phenylacetaldehyde (pDMBIP); veratrole, indole, phenylacetaldehyde, anethole and eugenol (VIPAE); trimethoxybenzene, indole, and cinnamaldehyde (TIC); trimethoxybenzene and indole (TI); trimethoxybenzene and cinnamaldehyde (TC); and quaiacol, indole and phenylacetaldehyde (GIP).

Alternately, constituted attractants for Diabrotica species according to the present invention are selected from the group consisting of the following mixtures: cinnamaldehyde indole (CI); β-ionone and indole (BI); and β-ionone and cinnamaldehyde (BC).

According to another aspect of the invention, compounds effective as attractants for southern corn rootworm include; meta-dimethoxybenzene, paradimethoxybenzene, indole, phenylacetaldehyde, trimethoxybenzene, 1,2,4-trimethoxybenzene, transcinnamaldehyde, allyl benzene, cinnamonitrile, 4-methoxy cinnamaldehyde, cinnamyl acetate, phenyl propionitrile, and phenyl ethanol. Particularly useful are unsubstituted phenylpropanoids having an unsaturated side chain, and having an aldehydic carbonyl group or a nitrile group at the free terminus of said side chain.

Compounds herein shown to be effective as attractants for western corn rootworm include: trimethoxybenzene, 1,2,4-trimethoxybenzene, indole, cinnamaldehyde, trans-cinnamaldehyde, β-ionone, estragole, trans-anethole, 4-methoxy-1-vinyl benzene, 4-methoxy-1-propyl benzene, 4-methoxybenzyl methyl ether, 4-methoxyphenyl ethyl ether, 4-methoxyphenyl acetonitrile, 4-methoxycinnamonitrile, cinnamonitrile, 4-methoxy cinnamaldehyde, 2-methoxy cinnamaldehyde, cinnamyl acetate, and cinnamyl alcohol. Particularly useful are phenylpropanoids having a para-methoxy group, having an unsaturated side chain, and having an aldehydic carbonyl group or nitrile group at the free terminus of the side chain.

Compounds herein shown to be effective as attractants for notrhern corn rootworm include: estragole, trimethoxybenzene, 1,2,4-trimethoxybenzene, cinnamaldehyde, trans-cinnamaldehyde, cinnamonitrile, cinnamyl alcohol, cinnamyl acetate as well as 4-methylphenylethanol, 4-chlorophenylethanol, 4-fluorophenylethanol, phenylethanol, phenylpropanol, 4-methoxyphenylethanol, 3-methoxyphenylethanol, 2-methoxyphenylethanol, 4-methoxyphenylpropanol, phenylethylamine, and phenylpropylamine. Particularly useful NCR attractants are phenyl-propanoids such as (1) phenyl alkanols having a para-methoxy group and a 2- or 3-carbon alkanol, (2) phenyl alkanols with 2- or 3-carbon side chains including the unsaturated cinnamyl alcohol; and (3) phenyl alkylamines with 2- or 3-carbon side-chains.

Compounds shown herein to have particularly long term (persistent) effectiveness as NCR attractants include: phenyl propanol, phenylethyl amine, and 4-methoxyphenylethanol.

Compounds herein shown to be effective as attractants for *Diabrotica cristata* include: guaiacol, estragole, trimethoxybenzene, 1,2,4-trimethoxybenzene, indole, cinnamaldehyde, trans-cinnamaldehyde, β-ionone, 4-methoxycinnamaldehyde, cinnamyl alcohol, and cinnamonitrile.

Attractant compounds and compositions of the invention attract both male and female rootworms and can be used with sticky traps and other types of insect traps at suitable attractive dosages, preferably ranging from approximately 1 mg to 100 mg per trap, although doses of 0.01 mg to 200 mg have been found to be effective, to attract hundreds of beetles per day. The VIP mixture attracts SCR adults at rates of 10 to 100 times greater than controls. The TIC mixture attracts WCR and SCR adults at rates of 10 to 100 times greater than controls. The CI mixture attracts WCR and SCR adults at rates of 10 to 100 times greater than controls. 4-Methoxycinnamaldehyde, 4-methoxycinnamonitrile, and β-ionone attract WCR at rates 10 to 100 times controls; cinnamyl alcohol attracts NCR at rates 5–20 times controls; and cinnamaldehyde and cinnamonitrile atrract SCR at rates 5–20 times controls.

4-Methylphenylethanol, 4-chlorophenylethanol, 4-fluorophenylethanol, phenylethanol, phenylpropanol, 4-methoxyphenylethanol, 3-methoxyphenylethanol, 2-methoxyphenylethanol, 4-methoxyphenylpropanol, phenylethylamine, and phenylpropylamine attract NCR at rates approximately 5–50 times controls.

Attractants according to the invention may be used to manipulate adult corn rootworm behavior for monitoring and controlling corn rootworm populations. Through the use of these lures, a totally new technology for corn rootworm control is possible. By using these attractants, individually or in combination, the presence, species distribution, and reproductive state of adult corn rootworms can be monitored and pest management decisions be made for the next season infestation. Moreover, these attractants are so potent that they can mobilize adult corn rootworm populations in large fields and attract them to specific sites where they can be destroyed by spraying limited areas with conventional insecticides.

Alternatively, these lures can be used as components of a toxic bait for adult beetles. The toxic bait comprises: i) a Diabrotica species attractant, ii) a compulsive feeding stimulant, and iii) a diabroticiticidal insecticide. These baits can combine: i) as attractant, either the multi-component mixtures, e.g., VIP or TIC mixtures and/or the single component lures, e.g., eugenol, indole, veratrole, cinnamaldehyde, cinnamonitrile, cinnamyl alcohol, cinnamyl acetate;, 4-methoxycinnamaldehyde, 4-methoxycinnamonitrile, 4-methoxy-1-vinylbenzene, β-ionone, trimethoxybenzene, phenylethanol, phenylpropanol, 4-methoxyphenyl ethanol, 4-methoxyphenyl propanol, phenylethylamine, phenylpropylamine and/or other compounds found in volatile fractions of blossoms of Cucurbita plants (the exact choice of lure depending on the relative economic importance of the three Diabrotica species); ii) as compulsive feeding stimulant, cucurbitacins obtained from, for example, bitter squash, and iii) as the diabroticiticidal insecticide, a relatively small dosage of a wide variety or conventional insecticides including organophosphorous, carbamate and pyrethroid insecticides, such as carbaryl, methomyl, isofenphos, malathion, and dimethoate. As used here the term diabroticiticidal includes a Diabrotica species insecticide and includes any and all compounds capable of killing Diabrotica species. (See, e.g., Canadian Patent 1,195,222 to R. L. Metcalf and A. M. Rhodes for the cucurbitacin-insecticide bait). This toxic bait combination of ingredients provides a long range and persistent (long term) attraction of beetles to a poison bait that acts as a contact feeding stimulant.

Other aspects and advantages of the present invention will be apparent upon consideration of the following detailed description thereof which includes numerous illustrative examples of the practice of the invention.

DETAILED DESCRIPTION

The following examples illustrate practice of the invention in the production of lures for attracting and controlling Diabrotics species. Specifically, the invention relates to lures comprising one or more compounds found in the volatile fraction of Cucurbita blossoms, or analogs thereof, alone or in combination with other lures, insecticides, and/or compulsive feeding stimulants.

Example 1 relates to the attraction of Diabrotica species to single-component and multi-component lures in corn fields.

Example 2 relates to the response of Diabrotica species (*D. cristata* and *D. barberi*) in a prairie habitat to eugenol analogs and to attractants for *D. v. virgifera* and *D. barberi*.

Example 3 relates to the evaluation of twenty-four compounds, including estragole and estragole analogues, as attractants.

Example 4 relates to the preparation and use of poison (toxic) baits containing cucurbitacins, volatile attractants and insecticides.

Example 5 relates to Cucurbita blossom aroma and Diabrotica rootworm beetle attraction.

Example 6 relates to the evaluation of seven compounds, including phenylethanol analogues, as attractants.

The examples which follow are for illustrative purposes only and are not intended in any way to limit the scope of the invention.

EXAMPLE 1

Single and Multicomponent Kairomonal Lures for Southern and Western Corn Rootworms The attraction of Diabrotica species to single-component and multicomponent lures was evaluated in corn fields. The field experiments on attraction of SCR and WCR adults were conducted in 0.405-ha (1-acre) plots of "Illini Xtra Sweet" corn grown on the University of Illinois South Farms at Urbana, Ill., over a two year period. Most of the tests were conducted in August to correspond with the peak silk-feeding and oviposition periods of corn rootworm adults in central Illinois. In both years, the sweet corn plot was adjacent to a 0.405-ha trap crop of C. maxima cultivar "Blue Hubbard", to provide high densitites of SCR and WCR adults in the corn plots (Howe, et al., Environ. Entomol., 5:745–751 (1976), Lampman, et al., J. Chem. Ecol., 13:959–975 (1987).

Attraction of Diabrotica species to volatile compounds was measured by the average number of beetles caught during a 24-h period on 1.0-liter cylindrical paper cartons (15.2 cm high, 27.9 cm circumference) which were evenly coated with clear insect adhesive, TangleTrap™ (Tanglefood Co., Grand Rapids, Mich.) The candidate attractants were applied by capillary micropiettes to cotton dental wicks (13 mm long by 6 mm diameter) that were previously impregnated with mineral oil to prolong volatilization. The chemicals were purchased from Aldrich Chemical Co., (Milwaukee, Wis.) and assayed by gas chromatography as >97% pure. Indole, a solid at ambient temperatures (m.p. 52–54° C.), was dissolved in glass-distilled acetone before dosing the cotton wicks. For dosage-acticity tests, the various components were mixed in equal quantities by weight and diluted to the appropriate dosage with acetone. Treated and untreated (control) wicks were attached to the top of the paper cartons with TangleTrap™ and the inverted traps were placed on 1-m-high posts between the sweet corn rows. Four replicates of each treatment and a control were conducted in a randomized complete block desgin. The sticky traps within a block (ca. 50-m row of corn) were 5–10 m apart (depending on the number of treatments in a particular test) and the blocks were 3 m apart. The traps were baited and placed in the field between 1000 and 1300 hours and beetle counts were taken after 24 h. The significance of treatments was determined by analysis of variance and the individual means were separated by Duncan's multiple range test (Statistical Package for Social Sciences (SPSS) (Nie, et al., SPSS: statistical package for the social sciences, 2nd ed. McGraw-Hill, N.Y. (1975)). Student's t test was used for comparisons of two means (Sokal, et al., Biometry, Freeman, San Francisco (1969). Significance levels were set at P=0.05 at all statistical analyses.

The initial field test in August of the first year evaluated the response of SCR and WCR adults of a mixture of veratrole (V), indole (I), phenylacetaldehyde (P), trans-anethole (A), and eugenol (E) (=VIPAE mixture), as well as to the individual components. Each component in the VIPAE mixture was present at a dosage of 20 mg per trap and was compared with the individual components at 100 mg per trap. The response of SCR and WCR adults to a range of VIPAE doses, 1–300 mg, was conducted on the following day. Fifty SCR adults were removed from each 100-mg VIPAE trap, and returned to the laboratory for sex determination. Additional analyses in August evaluated the reduction in trap catches produced by the sequential removal of the individual components from the VIPAE lure. After the primary components of the initial lure were determined, a modified multicomponent lure consisting of veratrole, indole, and phenylacetaldehyde (=VIP mixture) was compared with its individual components to determine whether the attraction of SCR adults was the result of interactive or additive factors. The attraction and synergistic response of SCR adults of the VIP mixture was verified by tests conducted in August of the following year.

The importance of the ortho-dimethoxy configuratoin of veratrole to the overall activity of the VIP mixture was demonstrated in early September of the first year and August of the second year using mixtures containing compounds chemically related to veratrole. In late August of the second year, the VIP mixture was compared with a mixture containing compounds structurally related to veratrole and phenylacetaldehyde. Two mixtures, VIP (veratrole, indole, and phenylacetaldehyde) and TIC (1,2,4-trimethoxybenzene, indole, and trans-cinnamaldehyde), were evaluated at doses ranging from 1 to 30 mg.

The VIPAE mixture caught 26 times more SCR adults than the control traps and was 3 times more active than the only other significant attractant, veratrole (Table 1).

TABLE 1

Mean number of southern corn rootworm (SCR) and western corn rootworm (WCR) per trap (±standard deviation), August, South Farms, Illinois.

| Treatment | SCR[a] | WCR[a] |
|---|---|---|
| Control (untreated) | 0.8 ± 0.5[a] (4%) | 2.3 ± 1.3[a] (34%) |
| Veratrole (V)[b] | 6.8 ± 3.6[b] (33%) | 1.5 ± 1.0[a] (22%) |
| Indole (I) | 2.3 ± 2.1[a] (11%) | 3.3 ± 2.1[a] (49%) |
| Phenylacetaldehyde (P) | 2.5 ± 1.9[a] (12%) | 1.8 ± 1.3[a] (26%) |
| trans-Anethole (A) | 1.5 ± 1.0[a] (7%) | 9.0 ± 4.3[b] (100%) |
| Eugenol (E) | 2.8 ± 2.8[a] (13%) | 2.8 ± 1.0[a] (41%) |
| VIPAE mixture[c] | 20.8 ± 12.2 (100%) | 2.0 ± 0.8[a] (29%) |

[a]Means in the same column followed by the same letter are not significantly different (P = 0.05; Duncan's (1955) multiple range test; Nie, et al. (1975)). Numbers in parentheses are the relative percent activity of the mean trap catch as compared with the highest mean value in a column.
[b]Single-compound baited traps were dosed at 100 mg per trap; n = 4
[c]Each component of the mixture was present at a dosage of 20 mg per trap; n = 4.

The SCR response to VIPAE exceeded the additive response that was expected, based on the stimulation of a single receptor type by each of the individual components. In contrast to the SCR response, fewer WCR adults were caught on the VIPAE-baited traps than on those baited with 100 mg of trans-anethole. Furthermore, SCR adults responded to the mixture in a concentration-dependent manner. WCR adults did not respond to the VIPAE mixture at any concentration; therefore, the activity of the lure was species-specific. Although both male and female SCR were present on the baited traps, the overall sex ratio, as taken from the four 100-mg VIPAE-baited was 4.6 males to 1.0 female (n=200). It was not determined whether the skewed sex ratio reflected a field bias or a distinct sexual preference. Single-component lures for NCR and WCR adults, such as eugenol, indole, and estragole, attract primarily females (Ladd, et al., J. Econ. Entomol., 78:844–847 (1985), Andersen, et al., J. Chem. Ecol., 13:681–699 (1986), Lampman, et al., J. Chem. Ecol., 13:959–975 (1987)).

Components of the VIPAE mixture were sequentially removed to evaluate their contribution to the overall activity of the multicomponent lure. Traps baited with VIPAE caught 27–30 times as many SCR adults as untreated controls, and all of the four-component mixtures caught significantly more beetles than the controls. However, the absence or veratrole from the VIPAE mixture resulted in a dramatic 77% reduction of SCR trap catch relative to the complete mixture. Although the mean trap catches were not significantly different, the removal of indole or phenylacetaldehyde from the VIPAE mixture produced 58 and 60% reductions in trap catches, respectively, whereas mixtures without trans-anethole or eugenol resulted in only 22 and 24% fewer beetles being caught, respectively. These results suggested the primary attractants in the VIPAE mixture to be veratrole, indole, and phenylacetaldehyde, and a comparison of the three-component VIP mixture with the five-component VIPAE mixture showed no significant difference in SCR trap catches between the two lures. Two-component mixtures without either phenylacetaldehyde, indole, or veratrole (VI, VP and IP mixtures) caught significantly fewer SCR adults than traps baited with VIPAE. A comparison of the VIP, VI, IP, and VP trap catches with their four- and five-component couterparts containing either anethole, eugenol, or both compounds (i.e., VIPAE, VIPA, and VIPE compared with VIP; IPAE with IP; VIAE with VI; and VPAE with VP) further supports the conclusion that anethole and eugenol were less important components of the original VIPAE mixture. WCR trap catches did not differ from the untreated controls in any of the tests conducted in the first year.

The VIP mixture was also compared with its individual components and several two-component mixtures. The VIP-baited traps caught ca. 8 times as many SCR adults as the mean additive response that would be expected based on the stimulation of different receptors by the individual components therefore, SCR adults respond to the multicomponent lure in an interactive and synergistic manner. SCR adults also exhibited synergistic responses to the two-component mixtures, VP and VI, although less than half as many beetles were attracted to these traps as compared with the VIP-baited traps.

The importance of veratrole to the overall activity of the VIP mixture was demonstrated by the reduction in trap catch with mixtures containing indole, phenylacetaldehyde, and either the meta- or para-isomer of veratrole (ortho-dimethoxybenzene). These mixtures caught 36 and 84% fewer SCR adults, respectively, than traps baited with the VIP mixture. The substitution of guaiacol (2-methoxyphenol) for veratrole in the VIP mixture also reduced trap catch-ca. 80% (Table 2). These data imply that the ortho-dimethoxy configuration is critical for beetle response to the mixture. The higher means SCR trap catches with VIP-baited traps in September, as compared with those in August of the first year, probably reflect a seasonal increase in trap catch which has also been documented for NCR and WCR adults (Ladd, *J. Econ. Entomol.*, 77:339–341 (1984), Andersen, et al., *J. Chem Ecol.*, 13:681–699 (1986), Lampman, et al., *J. Chem Ecol.*, 13:959–975 (1987)).

In the second year the attraction and synergistic response of SCR adults to the VIP mixture was verified. There were 14–50 times more SCR adults caught on VIP-baited traps than on untreated controls. Furthermore, the number of beetles captured with the multicomponent lure was 3–4 times greater than the expected mean additive trap catch based on the performance of the individual components (Table 2).

TABLE 2

Mean number of southern corn rootworms (SCR) and western corn rootworms (WCR) per trap (±standard deviation) baited with various candidate attractants, August, South Farms, Illinois.

| Treatment | SCR[a] | WCR[a] |
|---|---|---|
| August 1 | | |
| Control (untreated) | 1.8 ± 1.5 (2%) | 20.5 ± 4.2 (89%) |
| VIP[b] | 91.0 ± 19.7*[c] (100%) | 23.0 ± 11.3NS[d] (100%) |
| August 4 | | |
| Control (untreated) | 0.8 ± 1.0[a] (2%) | 12.5 ± 9.4[a] (24%) |
| Veratrole (V) | 5.8 ± 3.4[b] (15%) | 20.0 ± 5.7[a] (39%) |
| Indole (I) | 1.5 ± 1.0[ab] (4%) | 51.3 ± 24.4[b] (100%) |
| Phenylacetaldehyde (P) | 3.0 ± 1.2[b] (8%) | 17.8 ± 7.9[a] (35%) |
| Guaiacol (G) | 0.8 ± 0.6[a] (2%) | 20.0 ± 8.9[a] (39%) |
| GIP | 8.5 ± 7.4[ab] (21%) | 40.8 ± 8.1[b] (80%) |
| VIP | 39.8 ± 14.8[c] (100%) | 34.3 ± 7.8[ab] (67%) |
| August 7 | | |
| Control (untreated) | 2.0 ± 2.2[a] (4%) | 7.0 ± 2.2[a] (22%) |
| Veratrole (V) | 8.8 ± 2.1[b] (20%) | 18.5 ± 7.2[b] (59%) |
| Indole (I) | 2.8 ± 1.3[a] (6%) | 27.5 ± 11.8[bc] (87%) |
| Phenylacetaldehyde (P) | 5.3 ± 3.2[ab] (12%) | 13.3 ± 8.1[ab] (42%) |
| VIP | 45.0 ± 9.1[c] (100%) | 31.5 ± 9.7[c] (100%) |

[a]Means in the same column followed by the same letter are not significantly different (P = 0.05; Duncan's (1955) multiple range test; Nei, et al. (1975). Values in parentheses are the relative percent activity as compared with the highest mean value (100%) in the column for each test date.
[b]Each compound was present at a dosage of 20 mg per trap; n = 4.
[c]Mean followed by an asterisk is significantly different from control (P = 0.05; t test; df = 3)
[d]Mean followed by "NS" is not significantly different from control (P = 0.05; t test; df = 3).

Although chemical analyses of the floral components of Cucurbita blossoms and plant parts of *Zea mays* have revealed an extensive array of "green leaf volatiles", aromatic compounds, hydrocarbons, and terpenoids, the components of the VIP mixture apparently do no co-occur in anyone plant part (Buttery, et al., *J. Agric. Food Chem.*, 26:866–869 (1978), Buttery, et al., J. Agric. Food Chem., 26:771–774 (1980), Itokawa, et al., *Phytochemistry*, 21:1935–1937 (1982), Buttery, et al *J. Agric. Food Chem.*, 32:1104–1106 (1984), and Andersen, et al., *J. Chem. Ecol.*, 13:681–699 (1987). However, two related compounds, 1,2, 4-trimethoxybenzene and trans-cinnamaldehyde, are present, along with indole, in the blossom extracts of several *C. maxima* cultivars (Andersen, et al., *J. Chem. Ecol.*, 13:681–699 (1987); unpublished data). Two mixtures, VIP and TIC (1,2,4-trimethoxybenzene, indole, and trans-cinnamaldehyde), were compared for attraction of SCR adults and appeared similar for this species at any dosage (Table 3).

TABLE 3

Mean number of southern corn rootworm (SCR) and western corn rootworms (WCR) per trap (±standard deviation) for traps baited with either a) a mixture of veratrole, indole, and phenylacetaldehyde (VIP mixture) or b) 1,2,4-trimethoxybenzene, indole, and trans-cinnamaldehyde, (TIC mixture) over a range of dosages; August, South Farms, Illinois.

| Treatment | Dosage[a] (mg) | SCR[b] | WCR[b] |
|---|---|---|---|
| VIP mixture | 0[c] | 5.2 ± 4.8[a] (7%) | 2.7 ± 1.6[a] (17%) |
| | 1 | 6.2 ± 2.9[a] (9%) | 4.2 ± 4.8[a] (27%) |
| | 3 | 15.7 ± 8.2[b] (22%) | 4.7 ± 2.6[a] (30%) |
| | 10 | 37.7 ± 22.6[b] (52%) | 12.5 ± 3.3[b] (81%) |

TABLE 3-continued

Mean number of southern corn rootworm (SCR) and western corn rootworms (WCR) per trap (±standard deviation) for traps baited with either a) a mixture of veratrole, indole, and phenylacetaldehyde (VIP mixture) or b) 1,2,4-trimethoxybenzene, indole, and trans-cinnamaldehyde, (TIC mixture) over a range of dosages; August, South Farms, Illinois.

| Treatment | Dosage[a] (mg) | SCR[b] | WCR[b] |
|---|---|---|---|
| | 30 | 72.5 ± 20.2$^c$ (100%) | 15.5 ± 2.6 (100%) |
| TIC mixture | 0$^c$ | 5.2 ± 4.8$^a$ (7%) | 2.7 ± 1.6$^a$ (3%) |
| | 1 | 15.2 ± 11.9$^{ab}$ (20%) | 15.5 ± 2.5$^b$ (20%) |
| | 3 | 17.0 ± 8.5$^b$ (22%) | 36.0 ± 16.9$^c$ (47%) |
| | 10 | 59.0 ± 29.7 (78%) | 57.0 ± 16.2$^{cd}$ (74%) |
| | 30 | 76.0 ± 21.4$^c$ (100%) | 77.2 ± 21.3$^d$ (100%) |

[a]Dosage refers to the total amount of all components present; n = 4.
[b]Means followed by the same letter in a column are not significantly different (P = 0.05; Duncan's (1955) multiple range test; Nie, et al. (1975)) for a particular test. Values in parentheses are relative percent activity as compared with the value in the column with the highest mean trap catch (100%) for a particular test.
[c]Control.

The two multicomponent lures varied significantly in their attraction of WCR adults. The TIC-baited traps caught 5.7 times more WCR adults than controls at 1 mg per trap and 28.6 times more at 30 mg per trap, whereas the VIP-baited traps were not significantly different from controls at 1 mg per trap and were only 3.7 times greater than control WCR trap catch at 30 mg per trap (Table 3). The attraction of WCR adults to the VIP-baited traps at the higher dosages was probably due to the increased amount of indole per trap (Andersen, et al., J. Chem. Ecol., 12:687–699 (1986)) because the WCR trap catches with indole and the VIP mixture were not significantly different on two date in the second year (Table 2).

The VIP and TLC lures were active during the peak oviposition and silk-feeding periods of WCR and SCR adults; therefore, they can be useful to monitor or to attract beetles to a toxicant. Ongoing field studies have shown that the TIC lure can concentrate WCR and SCR at the edges of 2–4-ha field plots, thereby redefining the spatial distribution of the beetle within the agroecosystem and that the TIC lure attracts significantly more female WCR than males.

EXAMPLE 2

The Response of Diabrotica species (*D. cristata* and *D. barberi*) in a Prairie Habitat to Eugenol Analogs and Other Attractants for *D. v. virgifera* and *D. barberi*

The candidate lures in all experiments were purchased commercially and exceeded 98% purity. The test chemicals were applied by capillary micropipettes to cotton dental wicks which were attached to the tops of 1.0 liter cylindrical paper cartons covered with TangleTrap™ (Tanglefoot Co., Grand Rapids, Mich.). The sticky trap techniques used were as described in Example 1. Cinnamyl alcohol and para-methoxycinnamaldehyde, which are solids, were dissolved in glass-distilled acetone prior to dosing the cotton wicks. All treatments were applied at a dosage of 100 mg per trap. 1,2,4-trimethoxybenzene, indole, and trans-cinnamaldehyde were mixed in a ratio of 1:1:1, by weight, immediately prior to dosing the cotton wicks. Control traps had untreated cotton wicks. Four replicates of treated and untreated traps were randomly positioned 10 meters apart on top of 1 m high posts along the border of a eight foot wide strip cut through the middle of a 4.05 ha relict prairie at Trelease Woods (ca. two miles northeast of Urbana, Ill.). The field consisted primarily of *Andropogon gerardii* Vitman (big bluestem) and a variety of composites. The tests were conducted in mid-August of two years and were timed to coincide with the presence of *D. cristata* and *D. barberi* adults in the flower heads of Canada thistle (*Carduus arvensis* Robson). In the second year, several new attractants of *D. v. virgifera* and *D. barberi* were tested in Trelease Woods and along the edge of a 0.8 ha field of hybrid corn located at the Pomology South Farms, Urbana, Ill. Attraction of Diabrotica species to the various lures was measured by the mean number of beetles caught after 24-h. On one date in late August of the first year, *D. cristata* and *D. barberi* were removed from the traps and sexed in the laboratory. The significance of treatments in all tests was determined by an analysis of variance and the individual means were separated by Duncan's multiple range test (Statistical Package for Social Science, Nie, et al., SPSS: statistical package for the social sciences, 2nd ed. McGraw-Hill, New York (1975). Data were logarithmically transformed for statistical analysis and the means and standard deviations are presented for the untransformed data.

Counts in the flower heads of Canada thistle indicated both *D. cristata* and *D. barberi* adults were present in the prairie test site. *D. cristata* adults were not present in the corn field and *D. v. virgifera* adults displayed no affinity for Canada thistle. In the initial experiment with the candidate lures, traps baited with eugenol and isoeugenol caught significantly more adult *D. cristata* and *D. barberi* than methyl eugenol baited traps or the unbaited traps in the prairie habitat (Table 4).

TABLE 4

Mean number of Diabrotica species per sticky trap per day (±standard deviation) (Trelease Woods, Illinois).

| Treatment | D. barberi | D. cristata | D. v. virgifera | D. u. howardi |
|---|---|---|---|---|
| August 18 | | | | |
| Eugenol[a] | 21.8 ± 7.3$^b$ | 11.5 ± 8.6$^b$ | 0.3 ± 0.5$^a$ | 0.3 ± 0.5$^a$ |
| Isoeugenol | 31.8 ± 26.7$^b$ | 10.5 ± 12.6$^b$ | 0.0$^a$ | 0.0$^a$ |
| Methyl eugenol | 1.8 ± 1.7$^a$ | 1.8 ± 1.5$^a$ | 0.0$^a$ | 0.0$^a$ |
| Check | 2.8 ± 1.0$^a$ | 1.8 ± 1.7$^a$ | 0.3 ± 0.5$^a$ | 1.0 ± 1.4$^a$ |
| August 20 | | | | |
| Eugenol | 22.5 ± 13.2$^c$ | 15.5 ± 7.9$^c$ | 0 | 0.8 ± 0.5$^a$ |
| Isoeugenol | 22.0 ± 3.7$^c$ | 10.5 ± 2.4$^c$ | 0 | 0.5 ± 1.0$^a$ |
| Safrole | 0.25 ± 0.25$^a$ | 1.3 ± 1.9$^a$ | 0 | 0.0$^a$ |
| Methyl eugenol | 2.0 ± 1.4$^{ab}$ | 1.5 ± 1.7$^a$ | 0 | 0.3 ± 0.5$^a$ |
| Isoeugenol | 2.3 ± 3.9$^{ab}$ | 2.5 ± 3.1$^{ab}$ | 0 | 1.0 ± 0.8$^a$ |
| Guaiacol | 4.3 ± 2.1$^b$ | 6.0 ± 2.6$^b$ | 0 | 0.8 ± 1.0$^a$ |
| Check | 0.5 ± 0.6$^a$ | 0.5 ± 0.6$^a$ | 0 | 0.3 ± 0.5$^a$ |
| August 27 | | | | |
| Eugenol | 10.5 ± 4.8$^b$ | 3.5 ± 3.3$^b$ | 0 | 0.3 ± 0.5$^a$ |
| Estragole | 6.5 ± 3.7$^b$ | 5.3 ± 1.0$^b$ | 0 | 3.0 ± 2.8$^a$ |
| Isoeugenol | 8.5 ± 3.4$^b$ | 2.5 ± 1.7$^b$ | 0 | 0.5 ± 1.0$^a$ |
| TIC$^c$ | 10.3 ± 3.3$^b$ | 5.0 ± 4.3$^b$ | 0 | 19.0 ± 4.5$^b$ |
| Check | 0.0$^a$ | 0.0$^a$ | 0 | 0.3 ± 0.5$^a$ |

[a]Each candidate lure was present at a dosage of 100 mg per trap; n = 4.
[b]Means in the same column on the same date followed by the same letter are not significantly different (P = 0.05; Duncan's multiple range test; Nie, et al., [1975]).
[c]TIC = a 1:1:1 mixture by weight of 1,2,4-trimethoxybenzene, indole, and trans-cinnamaldehyde.

A subsequent comparison of eugenol with several analogs showed guaiacol also significantly attracted both Diabrotica species, albeit to a lesser extent than either eugenol or isoeugenol (Table 4). As previously found for *D. barberi* in corn agroecosystems (Ladd, *J. Econ. Entomol.*, 77:339–341 (1984)), compounds lacking the hydroxyl and methoxy groups, present on the eugenol-type analogs, were inactive for both species (Table 4). The sex ratios of the beetles on the eugenol traps were 16.6:1 (female:male) for *D. barberi* adults and 6.9:1 for *D. cristata* (n=60 for both species). The beetle catches on the control traps were so low a reliable estimate of field sex ratios was not determined. However, a comparison of control catches with treatment catches in (Yaro, et al., *Environ. Entomol.*, 16:126–128 (1987)) also indicates that eugenol and 2-methoxy-4-propylphenol are more active for *D. barberi* females than *D. cristata* females.

In the final test, estragole and a 100 mg mixture (1:1:1) of 1,2,4-trimethoxybenzene, indole, and trans-cinnamaldehyde (TIC mixture) were as active as eugenol or isoeugenol for attracting *D. barberi* and *D. cristata* (Table 4). The TIC mixture also attracted a significant number of *D. u. howardi*. These lures when tested in or along side corn fields are primarily attractants for *D. v. virgifera* adults. (Lampman, et al., *J. Econ. Entomol.*, 80:1137–1142 (1987)).

In the second year, estragole, β-ionone, the TIC mixture, 4-methoxycinnamaldehyde, cinnamyl alcohol and eugenol attracted more *D. cristata* than control traps in the prairie habitat (Table 5).

TABLE 5

Mean number of Diabrotica species per day (±standard deviation) in 1987 (Trelease Woods, Illinois)

| Treatment[a] | *D. barberi* | *D. cristata* | *D. v. virgifera* | *D. u. howardi* |
|---|---|---|---|---|
| August 11 | | | | |
| β-ionone | 0.3 ± 0.5[ab] | 17.3 ± 8.7[b] | 4.0 ± 0.8[b] | 0.3 ± 0.5[a] |
| Eugenol | 9.5 ± 8.3[bc] | 39.5 ± 9.4[c] | 0.3 ± 0.5[a] | 0.0[a] |
| Estragole | 1.0 ± 2.0[a] | 13.5 ± 4.1[b] | 0.3 ± 0.5[a] | 0.3 ± 0.5[a] |
| Cinnamyl alcohol | 16.5 ± 5.1[c] | 28.3 ± 5.3[c] | 0.0 | 0.3 ± 0.5[a] |
| 4-methoxy-cinnamalde-hyde | 1.0 ± 0.8[a] | 11.0 ± 6.7[b] | 8.5 ± 5.3[b] | 0.3 ± 0.5[a] |
| TIC[c] | 4.5 ± 1.3[b] | 18.3 ± 6.1[b] | 1.0 ± 0.8[a] | 15.8 ± 6.1[b] |
| Check | 0.5 ± 0.6[a] | 1.6 ± 1.0[a] | 0.5 ± 0.7[a] | 0.3 ± 0.5[a] |
| August 14 | | | | |
| β-ionone | 0.3 ± 0.5[a] | 5.3 ± 2.2[b] | 2.3 ± 1.3[b] | 0.0[a] |
| α-ionone | 0.3 ± 0.5[a] | 2.8 ± 2.1[a] | 0.0[a] | 0.0[a] |
| Eugenol | 8.3 ± 3.3[c] | 20.0 ± 8.4[cd] | 0.0[a] | 0.0[a] |
| Estragole | 4.0 ± 0.8[b] | 13.0 ± 4.2[c] | 0.3 ± 0.5[a] | 0.5 ± 0.7[a] |
| Methyl eugenol | 1.0 ± 1.4[a] | 4.5 ± 1.3[ab] | 0.0[a] | 0.3 ± 0.5[a] |
| Cinnamyl alcohol | 13.0 ± 12.8[bc] | 20.5 ± 1.3[d] | 0.0[a] | 2.8 ± 1.7[b] |
| Check | 0.3 ± 0.5a | 2.5 ± 1.9[a] | 0.0[a] | 0.3 ± 0.5[a] |

[a]Each candidate lure was present at a dosage of 100 mg per trap; n = 4.
[b]Means in the same column on the same date followed by same letter are not significantly different (P = 0.5; Duncan's multiple range test; Nie, et al. [1975]).
[c]TIC = a 1:1:1 mixture by weight of 1,2,4-trimethoxybenzene, indole, and trans-cinnamaldehyde.

Eugenol and cinnamyl alcohol consistently had higher trap catches of *D. cristata* than the other attractants. In addition to the attraction of *D. cristata*, β-ionone and para-methoxycinnamaldehyde caught significantly more *D. v. virgifera* than controls and the TIC mixture was an active lure for *D. u. howardi* (Table 5). Eugenol, cinnamyl alcohol, and the TIC mixture also attracted *D. barberi*; however, cinnamyl alcohol was ca. 3.5 times more active than the TIC mixture (Table 5). Estragole was a significant attractant for *D. barberi* in one test, but not in the other. Eugenol and cinnamyl alcohol were 2 and 5 times more active for *D. barberi* than estragole, respectively (Table 5). Although *D. barberi* and *D. cristata* respond in a similar fashion to eugenol analogs, both species are also attracted to compounds that are structurally distinct from eugenol, such as cinnamyl alcohol, β-ionone, and 4-methoxycinnamaldehyde. Methyl eugenol and α-ionone were inactive as attractants for any of the Diabrotica species in these tests.

A comparative study was conducted with several attractants for *D. barberi* and *D. v. virgifera* along the outside row of hybrid field corn. Cinnamyl alcohol and eugenol exhibited roughly equivalent activity for *D. barberi* (Table 6) as previously observed in the prairie tests (Table 5).

TABLE 6

Mean number of Diabrotica species per stick trap per day (±standard deviation) in corn (Pomology, South Farms, Illinois).

| Treatment | *D. barberi* | *D. v. virgifera* | *D. u. howardi* |
|---|---|---|---|
| August 7 | | | |
| Estragole[a] | 2.3 ± 2.1[ab] | 64.0 ± 15.9[b] | 7.0 ± 4.5[a] |
| Eugenol | 5.8 ± 2.2[b] | 10.0 ± 2.9[a] | 6.3 ± 1.0[a] |
| 4-methoxy-cinnamaldehyde | 0.3 ± 0.5[a] | 375.0 ± 50.0[d] | 1.5 ± 2.4[a] |
| Cinnamyl alcohol | 8.5 ± 6.1[b] | 13.8 ± 10.2[a] | 24.5 ± 13.6[b] |
| β-ionone | 0.5 ± 0.7[a] | 263.5 ± 94.6[cd] | 1.8 ± 2.4[a] |
| TIC[c] | 0.3 ± 0.5[a] | 212.5 ± 62.9[c] | 80.0 ± 27.1[c] |
| Check | 0.0[a] | 10.5 ± 3.7[a] | 5.3 ± 2.6[a] |
| August 18 | | | |
| Eugenol | 16.3 ± 5.7[b] | 2.8 ± 2.9[a] | 0.0[a] |
| β-ionone | 1.5 ± 1.0[a] | 89.0 ± 18.2[b] | 0.5 ± 0.7[a] |
| 4-methoxy-cinnamaldehyde | 1.0 ± 0.8[a] | 178.8 ± 32.0[c] | 0.0[a] |
| Cinnamyl alcohol | 23.3 ± 5.9[c] | 3.3 ± 2.7[a] | 1.8 ± 1.3[b] |
| Check | 0.8 ± 1.0[a] | 0.8 ± 0.5[a] | 0.3 ± 0.5[a] |

[a]Each candidate lure was present at a dosage of 100 mg per trap; n = 4.
[b]Means in the same column on the same date followed by the same letter are not significantly different (P = 0.05); Duncan's multiple range test; Nie, et al. (1975)).
[c]TIC = a 1:1:1 mixture by weight of 1,2,4-trimethoxybenzene, indole, and trans-cinnamaldehyde.

Cinnamyl alcohol was also active, albeit at a low level, for *D. u. howardi*. Estragole, β-ionone, the TIC mixture, and 4-methoxycinnamaldehyde were highly active attractants for *D. v. virgifera*, but not *D. barberi*, when tested along the corn field. The TIC mixture also caught significantly more *D. u. howardi* than control traps (Table 6). *D. cristata* adults were never found in any of the treatment or control traps in the corn tests. Although the TIC mixture and estragole exhibited activity for *D. barberi* in the prairie tests, they were not active for this species in the corn tests which agrees with previously published data for this species (Ladd, *J. Econ. Entomol.*, 77:339–341 (1984), Lampman, et al., *J. Econ. Entomol.*, 80:1137–1142 (1987), Lampman, et al., *J. Chem. Ecol.*, 13:959–975 (1987).

Geographical variation in the response of *D. barberi* and *D. cristata* to eugenol is apparently minimal based on the similar attraction to eugenol analogs recorded in central Illinois, Ohio, (Ladd, J. Econ. Entomol., 77:339–341 (1984) and in South Dakota (Yaro, et al., *Environ. Entomol.*, 16:126–128 (1987). Although the two species responded identically to eugenol and two chemical analogs in a previous test (Yaro, et al., supra), the data presented here demonstrates that *D. cristata* also shares some chemosensory adaptations with *D. v. virgifera*. In the prairie tests, *D. cristata* was moderately attracted to β-ionone and 4-methoxycinnamaldehyde, whereas *D. barberi* adults did not respond to these compounds. These same compounds were potent attractants of *D. v. virgifera* when evaluated in corn field tests. Female *D. barberi* also appear more responsive to eugenol-type lures than female *D. cristata* (Yaro, et al., supra). Even though *D. cristata* responds to attractants for *D. v. virgifera,* the highest trap catches in this study were with attractants for *D. baberi* (i.e., eugenol and cinnamyl alcohol). The attraction of *D. barberi* and *D. cristata* to cinnamyl alcohol in prairie and corn habitats was unexpected, as previous tests had shown attractants for *D. barberi* require a methoxy and hydroxy group on a phenyl ring with a three-carbon side chain (Ladd, *J. Econ. Entomol.,* 77:339–341 (1984), Lampman, et al., *J. Chem. Ecol.,* 13:959–975 (1987)). Both Diabrotica species responded to compounds that lacked these structural moieties (i.e., cinnamyl alcohol, para-methoxycinnamaldehyde, and β-ionone).

All of the Diabrotica species examined to date are attracted to chemically related cyclic compounds, however, each species displays a distinctive pattern of response when exposed to a broad spectrum of candidate lures. The adaptation of *D. cristata* and *D. barberi* to eugenol-type analogs may have arisen in a Nearctic ancestor as conjectured by Yaro, et al., supra; however, the attraction of Diabrotica species from two distinct taxonomic groups (*fucata* and *virgifera* (Wilcox, Coleopterorum Catalogus Supplementa (Chrysomelidae: Galerucinae, Luperini), Pars 78, Fasc. 3. 2nd ed. Dr. W. Junk, s'Gravenhagen, Netherlands, 1972) to a variety of structurally related compounds suggest the chemosensory response to phenylpropanoid and cyclic semiochemicals is of older evolutionary origin, perhaps parallel to the generalized response of this group to cucurbitacins (Metcalf, *J. Chem. Ecol.,* 12:1109–1124 (1986)). In this regard, it is interesting that attractants for *D. barberi, D. cristata, D. v. virgifera,* and *D. u. howardi* (such as cinnamyl alcohol, β-ionone, and the components of the TIC mixture) have been isolated from the floral volatiles of *Cucurbita maxima* cultivars (Andersen, *J. Chem. Ecol.,* 12:687–699 (1986), Metcalf & Lampman unpublished data). Furthermore, *D. barberi, D. virgifera,* and *Acalymma vittata,* the striped cucumber beetle, are attracted to sticky traps baited with flowers from "Blue Hubbard", a cultivar of *C. maxima* (McAuslane, et al., *Proc. Entomol. Soc. Ont.,* 117:49–57 (1986), Metcalf & Lampman unpublished data). An evaluation of the olfactory responses of additional Diabrotica species, particularly those with different host plant affinities and geographical distributions, to a variety of semiochemicals and volatile constituents of the host plants of adults, may further elucidate the adaptive significance of the chemosensory response to these natural products and the evolution of chemoreception in this group.

EXAMPLE 3

Evaluation of Twenty-four Compounds Including Estragole and Estragole Analogues as Attractants Six of the twenty-four chemical compounds evaluated as attractants were prepared as described. 4-methoxy-1-propylbenzene (IV, Table 1) was prepared from 4-propylphenol and dimethylsulfate, b.p. 215–216° C., lit. 210–214° C. (Klages, *Ber. Deut. Chem. Gesell.,* 32:1437–1441 (1899)). 4-methoxybenzyl methyl ether (V) was prepared from 4-methoxybenzyl alcohol and dimethyl sulfate, b.p. 128–130°/30 mm, lit. 107–108/15 mm (Anglande, *Compt. Rend. Acad. Sci.,* 210:52–54 (1940)). 4-methoxyphenyl ethyl ether (VI) was prepared from 4-methoxyphenol and diethyl sulfate, m.p. 34–5°, lit. 36–7° (Robinson, et al., *J. Chem. Soc.,* 1926:392–401 (1926)). 4-methoxycinnamaldehyde (XI) was prepared from anisaldehyde and acetaldehyde, m.p. 58° (Vorlander, et al., *J. Prakt. Chem.,* 229:237–247 (1929)). 4-methoxycinnamic acid methyl ester (XIV) was prepared from the acid and anhydrous methanol, m.p. 87–89°, lit. 89° (Perkin, *J. Chem. Soc.,* 34:409–452 (1881)). 4-(4'-methoxyphenyl)-3-butene-2-one (XVI) was obtained from 4-methoxybenzaldehyde and acetone, m.p. 72–3°, lit. 72–3° (Einhorn, et al., *Justus Liebig's Ann. Chem.,* 243:362–378 (1888)). These compounds were all >98% pure as determined by gas chromatography-mass spectrometry. The remaining 18 chemicals described in the tables were purchased from Aldrich Chemical Co., Milwaukee, Wisc. and were 97–99% pure.

Test chemicals were applied by capillary micropipettes to cotton dental wicks that were attached to tops of 1.0 liter cylindrical paper cartons covered with TangleTrap™, Grand Rapids, Mich. The trapping techniques used were as previously described in Example 1. Cinnamyl alcohol, 4-methoxycinnamaldehyde, cinnamyl acetate, and 4-(4'methoxyphenyl)-3-butene-2-one which are solids at ambient temperature were prepared as standard w/v solutions in acetone prior to dosing the cotton wicks. All treatments were made at a dosage of 100 mg or 100 μL of attractant per trap. Control traps had untreated wicks. Four replicates of treated and untreated traps were positioned randomly 10 meters apart on top of 1 m high posts along the edges of 25–50 ha. fields of hybrid corn (*Zea mays*), infested with adult NCR, SCR, and WCR beetles. Several experiments detailed in the Tables were made in a 0.4 ha plot of sweet corn (Illini X-tra Sweet).

Attraction of Diabrotica species adults of the sticky traps was measured by the mean number of beetles caught after 1 day (ca. 24 hours) exposure. The significance of the treatments was determined by analysis of variance and the individual means were separated by Duncan's multiple range test (Statistical Package for the Social Sciences, Nie, et al., 2nd. ed. McGraw-Hill, New York (1975). The data was logarithmically transformed for statistical analysis. Means and standard deviations are presented for the untransformed data. Significance levels were set at P=0.05 for all statistical analyses.

The response of WCR adults in corn to sticky traps baited with estragole or 4-methoxy-1-allylbenzene (I) and 7 analogues combining para-methoxyphenyl moieties with 2 and 3 atom side chains is shown in Table 7.

TABLE 7

Mean number of western corn rootworms (WCR) per sticky trap (±standard deviation) after 24 hours (South Farms, Illinois).

| | WCR per sticky trap | |
| --- | --- | --- |
| Treatment[a] | July 30 | August 29 |
| Control (untreated) | 31.7 ± 5.1[ab] (38%)[c] | 6.2 ± 2.1[a] (4%) |
| I. 4-CH$_3$OC$_6$H$_4$CH$_2$CH=CH$_2$ (estragole) (4-methoxy-1-allylbenzene) | 82.1 ± 8.6[b] (100%) | 147.2 ± 46.5[d] (100%) |
| II. 4-CH$_3$OC$_6$H$_4$CH=CHCH$_3$ trans-anethole (4-methoxy-2-propenylbenzene) | 48.0 ± 23.3[a] (58%) | NT |
| III. 4-CH$_3$OC$_6$H$_4$CH$_2$=CH$_2$ (4-methoxy-1-vinyl benzene) | 32.2 ± 13.5[a] (40%) | 21.5 ± 6.5[c] (15%) |

TABLE 7-continued

Mean number of western corn rootworms (WCR) per sticky trap (±standard deviation) after 24 hours (South Farms, Illinois).

|  | WCR per sticky trap | |
|---|---|---|
| Treatment[a] | July 30 | August 29 |
| IV. 4-CH$_3$OC$_6$H$_4$CH$_2$CH$_2$CH$_3$ (4-methoxy-1-propylbenzene) | 30.5 ± 11.0[a] (37%) | NT |
| V. 4-CH$_3$OC$_6$H$_4$CH$_2$OCH$_3$ (4-methoxy benzyl methyl ether) | 37.7 ± 23.4[a] (46%) | 46.7 ± 29.6[c] (32%) |
| VI. 4-CH$_3$OC$_6$H$_4$OCH$_2$CH$_3$ (4-methoxyphenyl ethyl ether) | 32.0 ± 8.4[a] (39%) | 12.0 ± 1.8[b] (8%) |
| VII. 4-CH$_3$OC$_6$H$_4$CH$_2$CN (4-methoxyphenyl acetonitrile) | 37.5 ± 8.4[a] (46%) | 114.5 ± 83.4[d] (78%) |

[a]Each candidate lure was tested at 100 mg per trap; n = 4.
[b]Means in the same column followed by the same letter on the same data are not significantly different (P = 0.05; Duncan's [1955] multiple range test; Nie, et al. [1975]).
[c]Relative percent activity as compared with the highest mean in each column.
[d]Not tested on that date.

Estragole is an effective kairomonal attractant for WCR adults in corn. Lampman, et al., *J. Chem. Ecol.*, 13:959–975 (1987). Attraction of WCR adults decrease markedly with a shift in the position of the C═C bond from 1-propenyl to 2-propenyl as in trans-anethole (II), and is lost through saturation of the double bond to 4-methoxy-1-propylbenzene (IV) (Table 7). Substitution of an oxygen atom for carbon in the side chain, as in 4-methoxyphenyl ethyl ether (VI), resulted in loss of attraction and activity was only marginally retained in 4-methoxybenzyl methyl ether (V) (Table 7). These changes suggest that the interaction of estragole with the WCR antennal receptors is unusually specific, as attractant studies with methyl eugenol and the oriental fruit fly have shown that highly attractive bioisosteric molecules can be formed by saturation of the C═C bond in the naturally occurring kairomone or by substitution of oxygen atoms (Mitchell, et al., *Environ. Entomol.*, 14:176–181 (1985). The intermediate attractivity of 4-methoxyphenylacetonitrile (VII) (Table 1) and the slight attractivity of 4-methoxy-1-vinylbenzene (III) supports the necessity of a 3 atom unsaturated side chain.

Role of methoxy group. The data in Table 8 demonstrate that a para-methoxy phenyl group is important for the specific attraction of WCR adults.

TABLE 8

Mean number of western (WCR) and souther (SCR) corn rootworm adults per sticky trap (±standard deviation) after 24 hours (South Farms, Illinois).

|  | August 5 first year | | August 4 second year | |
|---|---|---|---|---|
| Treatment[a] | WCR | SCR | WCR | SCR |
| control (untreated) | 0.7 ± 0.9[ab] | 17.5 ± 18.3[a] | 19.2 ± 8.9[a] | 1.0 ± 1.4[a] |
| I. 4-CH$_3$OC$_6$H$_4$CH$_2$CH═CH$_2$ (estragole) (4-methoxy-1-allylbenzene) | 17.2 ± 7.8[c] | 9.2 ± 5.6[a] | 84.5 ± 19.7[d] | 7.2 ± 5.1[a] |
| VIII. C$_6$H$_5$CH$_2$CH═CH$_2$ (allylbenzene) | 1.0 ± 0.8[a] | 24.7 ± 16.9[a] | 10.0 ± 1.4[a] | 12.4 ± 7.2[b] |
| IX. 4-CH$_3$OC$_6$H$_4$CH═CHCN (4-methoxycinnamonitrile) | 59.0 ± 32.1[d] | 6.5 ± 3.0[a] | 196.0 ± 145.3[de] | 4.0 ± 2.2[ab] |
| X. C$_6$H$_5$CH═CHCN (cinnamonitrile) | 1.5 ± 6.6[ab] | 156.0 ± 37.2[c] | 32.7 ± 11.4[bc] | 59.5 ± 49.0[c] |
| XI. 4-CH$^3$OC$_6$H$_4$CH═CHC(O)H (4-methoxycinnamaldehyde) | 143.7 ± 75.3[e] | 42.7 ± 27.6[b] | 204.7 ± 34.6[e] | 9.0 ± 6.5[b] |
| XII. C$_6$H$_5$CH═CHC(O)H (cinnamaldehyde) | 4.0 ± 1.8[b] | 431.2 ± 120.3[d] | 32.2 ± 8.5[b] | 135.5 ± 29.3[d] |
| XIII. 2-CH$_3$OC$_6$H$_4$CH═CHC(O)H (2-methoxycinnamaldehyde) | NT[c] | NT | 53.0 ± 14.7[c] | 12.2 ± 9.9[b] |

[a]Each candidate lure was tested at 100 mg per trap; n = 4.
[b]Means in the same column followed by the same letter on the same date are not significantly different (P = 0.05; Duncan's [1955] multiple range test; Nie, et al. [1975]).
[c]Not tested on that date.

The unsubstituted compounds, allylbenzene (VIII), cinnamonitrile (X) and cinnamaldehyde (XII), were unattractive or only weakly attractive to WCR adults. However, cinnamonitrile (X) and cinnamaldehyde (XII) were highly attractive to SCR adults, the latter being the most effective attractant yet found for this species. Conversely, estragole or 4-methoxy-1-allylbenzene (I), 4-methoxycinnamonitrile (IX), and 4-methoxycinnamaldehyde (XI) were highly attractive to WCR (Table 8). Experiments with pairs of candidate attractants with and without para-methoxy groups were repeated on several occasions with similar results (Table 9).

TABLE 9

Mean number of western (WCR) and southern (SCR) corn rootworm adults per sticky trap (±standard deviation) after 24 hours on September 11 (South Farms, Illinois).

| Treatment[a] | WCR | SCR |
|---|---|---|
| Control (untreated) | 0.3 ± 0.5[ab] | 1.7 ± 1.3[ab] |
| XI. 4-$CH_3OC_6H_4CH$=$CHC(O)H$ (4-methoxycinnamaldehyde) | 22.2 ± 23.1[b] | 1.5 ± 1.3[ab] |
| XII. $C_6H_5CH$=$CHC(O)H$ (cinnamaldehyde) | 1.3 ± 1.3[a] | 24.0 ± 10.5[c] |
| XIV. 4-$CH_3OC_6H_4CH$=$CHC(O)OCH_3$ (4-methoxycinnamic acid methyl ester) | 1.0 ± 1.1[a] | 0.7 ± 1.5[a] |
| XV. $C_6C_5CH$=$CHC(O)OCH_3$ (cinnamic acid methyl ester) | 1.7 ± 1.7[a] | 3.2 ± 1.7[ab] |
| XVI. 4-$CH_3OC_6H_4CH$=$CHC(O)CH_3$ (4-methoxy phenyl-3-butene-2-one ketone) | 2.0 ± 3.7[a] | 1.0 ± 0.8[a] |
| XVII. $C_6H_5CH$=$CHC(O)CH_3$ (phenyl-3-butone-2-one ketone) | 0.0 | 5.0 ± 3.7[b] |

[a]Each candidate lure was tested at 100 mg per trap; n = 4.
[b]Means in the same column followed by the same letter on the same date are not significantly different (P = 0.05; Duncan's (1955) multiple range test; Nie, et al. (1975)).

Shifting the position of the methoxy group to 2-methoxycinnamaldehyde (XIII) (Table 8) resulted in a substantial decrease in attraction for WCR. This information suggests that WCR adults are evolutionarily attuned for maximal response to phenylpropanoid kairomones with para-methoxy groups, e.g., estragole, in contrast to SCR adults that respond to unsubstituted phenylpropanoid moieties, e.g., cinnamaldehyde.

Role of C=C unsaturation. Most of the kairomonal attractants for WCR, SCR, and NCR have side chains incorporating a C=C double bond, e.g., estragole and anethole for WCR (Lampman, et al., J. Chem. Ecol., 13:959–975 (1987)), eugenol and isoeugenol for NCR (Ladd, J. Econ. Entomol., 77:339–341 (1984)) and cinnamaldehyde for SCR (Tables 7, 9, 10). Saturation of the C=C bond of estragole, as in 4-methoxy-1-propylbenzene (IV), eliminated attraction for WCR (Table 7) and saturation of cinnamaldehyde as in phenylpropanaldehyde (XXII) substantially decreased attraction to SCR and WCR (Table 10). This requirement for an unsaturated side chain does not appear to be clear cut for NCR, as (Ladd, J. Econ. Entomol., 77:339–341 (1984)) found that the saturated analogue of eugenol, 2-methoxy-4-propylphenol, was approximately as attractive as eugenol or isoeugenol for this species.

Importance of carbonyl groups. The data of Table 3 shows the influence of three types of carbonyl (C=O) containing groups on the attraction of WCR and SCR. Only the aldehydes, C(O)H (XI and XII) were attractive to either WCR or SCR respectively, and the esters C(O)$OCH_3$ (XIV and XV) and the ketones C(O)$CH_3$ (XVI and XVII) were unattractive to either species. The nitriles (IX and X) provide interesting examples of bioisosterism with aldehydes (XI and XII) (Table 2), as 4-methoxycinnamonitrile (IX) was almost as attractive as 4-methoxycinnamaldehyde (XI) to WCR, and cinnamonitrile (X) approached cinnamaldehyde (XII) in attractivity to SCR. Saturation of the C=C bond of cinnamonitrile, as in phenylpropionitrile (XXIII), decreased attractivity to both WCR and SCR (Table 10).

Cinnamyl alcohol as an NCR attractant. The species specific attraction of Diabrotica species to phenylpropanoids is apparently associated with the nature of the phenyl substitution, e.g., para-methoxy for WCR, unsubstituted for SCR, and 3-methoxy-4-hydroxy for NCR (Ladd, et al., J. Econ. Entomol., 76:1049–1051 (1983), Ladd, J. Econ. Entomol., 77:339–341 (1984), Lampman, et al., J. Chem. Ecol., 13:959–975 (1987), Lampman, et al., Environ. Entomol., in press (1988)). Neither cinnamaldehyde (XII) nor cinnamonitrile (X) were significantly attractive to NCR adults (Table 10). Therefore, the marked attractivity of cinnamyl alcohol (XVIII) to this species (Tables 10, 11) was unexpected and demonstrates another facet of singularities of phenylpropanoid attraction to the three rootworm species. Cinnamyl acetate (XIX) was also moderately attractive to NCR although it was not attractive to SCR or WCR (Table 10). SCR adults were weakly attracted to cinnamyl alcohol in one test (Table 11). Both cinnamic acid (XX) and its methyl ester (XXI) were also unattractive to all three species of rootworms (Table 10). Further evaluation (Table 11) showed that cinnamyl alcohol (XVIII) was as attractive to NCR as was eugenol and this result was corroborated several times during August and September (Lampman, et al., Environ. Entomol., in press (1988)).

TABLE 10

Mean number of western (WCR), southern (SCR), and northern (NCR) corn rootworms per sticky trap after 24 hours on August 5 (South Farms, Illinois).

| Treatment[a] | WCR | SCR | NCR |
|---|---|---|---|
| Control (untreated) | 9.0 ± 4.2[ab] | 2.2 ± 1.3[a] | 1.0 ± 0.8[a] |
| XII. $C_6H_5CH$=$CHC(O)H$ (cinnamaldehyde) | 44.5 ± 25.5[d] | 67.5 ± 23.1[d] | 1.2 ± 1.3[a] |
| X. $C_6H_5CH$=$CHCN$ (cinnamyl nitrile) | 37.8 ± 7.8[cd] | 47.5 ± 15.4[cd] | 0.3 ± 0.5[a] |
| XVIII. $C_6H_5CH$=$CHCH_2OH$ (cinnamyl alcohol) | 16.5 ± 1.9[ab] | 14.5 ± 9.6[ab] | 8.7 ± 4.6[c] |
| XIX. $C_6H_5CH$=$CHCH_2OC(O)CH_3$ (cinnamyl acetate) | 24.0 ± 1.07[b] | 6.0 ± 1.5[a] | 5.7 ± 2.9[b] |
| XX. $C_6H_5CH$=$CHC(O)OH$ (cinnamic acid) | 12.7 ± 4.9[a] | 1.7 ± 0.5[a] | 1.7 ± 1.0[a] |
| XXI. $C_6H_5CH$=$CHC(O)OCH_3$ (cinnamic acid, methyl ester) | 9.5 ± 4.5[a] | 2.0 ± 0.8[a] | 0.5 ± 0.6[a] |
| XXII. $C_6H_5CH_2CH_2C(O)OH$ (dihydrocinnamic acid) | 12.0 ± 3.6[a] | 33.7 ± 8.7[bc] | 4.0 ± 1.4[b] |
| XXIII. $C_6H_5CH_2CH_2CN$ (phenyl propionitrile) | 12.0 ± 4.2[a] | 23.7 ± 9.7[b] | 0.3 ± 0.5[a] |

[a]Each candidate lure was tested at 100 mg per trap; n = 4.
[b]Means in the same column followed by the same letter on the same date are not significantly different (P = 0.05; Duncan's (1955) multiple range test; Nie, et al. (1975)).

4-methoxycinnamaldehyde (XI) proved to be unattractive to both NCR and SCR (Table 11).

TABLE 11

Mean number of western (WCR), souther (SCR), and northern (NCR) corn rootworms (±standard deviation) per sticky trap after 24 hours (South Farms, Illinois).

| Treatment[a] | August 7 | | | August 18 | | |
|---|---|---|---|---|---|---|
| | WCR | SCR | NCR | WCR | SCR | NCR |
| Control (untreated) | $10.5 \pm 3.7^{ab}$ | $5.2 \pm 2.6^a$ | $0.0^a$ | $0.8 \pm 0.5^a$ | $0.3 \pm 0.5^a$ | $0.8 \pm 1.0^a$ |
| XI. 4-$CH_3OC_6H_4CH$=CHC(O)H (4-methoxycinnamaldehyde) | $375.0 \pm 50.0^c$ | $1.5 \pm 2.4^a$ | $0.0^a$ | $178.7 \pm 31.9^b$ | $0.0^a$ | $1.0 \pm 0.8^a$ |
| XVIII. $C_6H_5CH$=$CHCH_2OH$ (cinnamyl alcohol) | $13.8 \pm 10.2^a$ | $24.5 \pm 13.6^b$ | $8.5 \pm 6.1^b$ | $3.3 \pm 1.7^a$ | $1.8 \pm 1.3^b$ | $23.2 \pm 5.9^c$ |
| XXIV. 3-$CH_3O$, 4-OH, $C_6H_3CH_2CH$=$CH_2$ (eugenol) | $10.0 \pm 2.9^a$ | $6.2 \pm 1.0^a$ | $5.7 \pm 2.2^b$ | $2.7 \pm 2.9^a$ | $0.0^a$ | $16.5 \pm 5.7^b$ |
| I. 4-$CH_3OC_6H_4CH_2CH$=$CH_2$ (estragole) (4-methoxy-1-allylbenzene) | $64.0 \pm 15.9^b$ | $7.0 \pm 4.5^a$ | $2.2 \pm 2.1^{ab}$ | NT | NT | NT |
| XII. $C_6H_5CH$=CHC(O)H (cinnamaldehyde) | $61.5 \pm 15.6^b$ | $63.5 \pm 25.7^c$ | $0.3 \pm 0.5^a$ | NT | NT | NT |

[a]Each candidate lure was tested at 100 mg per trap; n = 4.
[b]Means in the same column followed by the same letter on the same date are not significantly different (P = 0.05; Duncan's (1955) multiple range test; Nie, et al. (1975)).

4-methoxycinnamaldehyde as a WCR attractant. This compound (XI, Table 8) is a very effective kairomonal attractant for WCR adults, but is essentially unattractive to NCR and SCR adults (Tables 8, 9, 11). It is however, attractive to the closely related *Diabrotica cristata* (Harris) (Lampman, et al., *Environ. Entomol.,* in press (1988)). Cylindrical sticky traps baited with logarithmically decreasing amounts of 4-methoxycinnamaldehyde were used to determine the limit of response (LR) for attraction of WCR adults in corn. Significant attraction was obtained with 4-methoxycinnamaldehyde present on cotton wicks at 0.03 mg, the approximate LR value. Similar experiments with other WCR kairomonal attractants determined LR values for indole of 1 mg (Andersen, et al., *J. Chem. Ecol.,* 12:687–699 (1986)) and estragole of about 3 mg (Lampman, et al., *J. Chem. Ecol.,* 13:959–975 (1987)). Thus 4-methoxycinnamaldehyde is about 100-fold more effective than these previously described WCR attractants, and its activity approaches that of the WCR female sex pheromone 8-methyl-2-decylpropanoate which attracted male WCR at 5 ug per sticky trap (Andersen, et al., *J. Chem. Ecol.,* 12:687–699 (1986)). Unlike the sex pheromone, 4-methoxycinnamaldehyde is effective in attracting both male and female WCR and the combined male/female sex ratio of beetles trapped during August and September of the second year varied from 0.2 to 1.3. Thus this kairomone can be useful for attracting WCR to poison baits for control just prior to oviposition. 4-methoxycinnamaldehyde was used routinely to monitor WCR populations during the summer of the second year and consistently attracted several times as many WCR adults as did estragole at equivalent dosages (see Table 8).

In experiments to determine the longevity of attraction, wicks treated with 100 mg of 4-methoxycinnamaldehyde were transferred to fresh sticky traps daily and the 24 hour trap catch determined. The original treated wicks remained highly attractive over a 16 day period of exposure to August sunlight and through two heavy rainstorms.

4-methoxycinnamaldehyde has been identified as a constituent of the essential oils of a variety of plants, e.g., *Agastache rugosa* (Fujita, et al., Nippon Kagaku Zasshi, 78:1541–1542 (1957); *Chem. Absts.,* 53:22754 (1959)), *Orthodon methylchavicoliferum* (Ueda, et al., Nippon Kagaku Zasshi, 77:1308–1310 (1956); *Chem. Absts.,* 53:22754g (1959)), and *Ocimum basilicum* (Pogany, et al., *Perfume Essential Oil Rev.,* 59:558–865.t (1968)) all of the family Lamiaceae;*Acorus gramineus* (Araceae, Fujita, et al., Yakugaku Zasshi, 91:132–133 (1971); *Chem. Absts.,* 74:130278k (1971)), *Artemesia dracunculus* (Carduaceae, Thieme, et al., *Pharmazie,* 27:255–265 (1972)), *Limnophila rugosa* (Scropulariaceae, Argwal, et al., *Ind. J. Pharmacol.,* 37:99–100 (1975)) and *Sphaeranthus indicus* (Compositae, Baslac, *Perfumery Essential Oil Record,* 50:765–768 (1959)). The presence of 4-methoxycinnamaldehyde in these essential oils was consistently associated with the presence of much larger quantities of estragole.

Species-specific attraction to phenylpropanoids. All of the Diabrotica species studied are attracted to structurally related phenylpropanoids and several synthetic derivatives. Within the spectrum of response to these compounds there are both specific responses to individual compounds and significant overlaps in the patterns of response among the several species. Species specific attraction is associated with two major alterations in phenylpropanoid structures: first, the nature of the substituents on the phenyl ring where 4-methoxy provides maximal attraction to WCR, as in estragole (Lampman, et al., *J. Chem. Ecol.,* 13:959–975 (1987)), and 3-methoxy-4-hydroxy provides maximal attraction to NCR, as in eugenol (Ladd, et al., *J. Econ. Entomol.,* 76:1049–1051 (1983); Ladd, *J. Econ. Entomol.,* 77:339–341 (1984)). The feral *D. cristata* appears to represent an intermediate type of response in preferring eugenol but also in responding to several WCR attractants (Lampman, et al., *Environ. Entomol.,* in press (1988)). The second important structural modification is the nature of the unsaturated side chain where both WCR and SCR respond most strongly to be unsaturated aldehyde and NCR to the unsaturated alcohol. Here again, *D. cristata* is strongly attracted to cinnamyl alcohol but also displays a significant response to the WCR attractant, 4-methoxycinnamaldehyde (Lampman, et al., *Environ. Entomol.,* in press (1988)). It is interesting that all four species of Diabrotica show significant attractant response to the mixture of squash blossom volatiles, 1,2,4-trimethoxybenzene, indole, and cinnamaldehyde (TIC) (Lampman, et al., *J. Econ. Entomol.,* 80:1137–1142 (1987); Lampman, et al., *Environ. Entomol.,* in press (1988)).

EXAMPLE 4

Preparation and Use of Poison Baits Containing Cucurbitacins, Volatile Attractants and Insecticides This example relates to the use of cucurbitacins, powerful feeding stimulants which are not volatile and therefore ineffective as long-range attractants, in combination with volatile attractants, such as eugenol, indole and veratrole in poison baits which greatly enhance the distance over which the baits act. A determination of optimal bait formulation, choice of insecticide, rate of application, and mode of application for efficient use to control adult corn rootworms was made.

The oxygenated tetracyclic triterpenoid cucurbitacins, bitter and toxic substances characteristic of the cucurbitaceae, mediate a classic example of co-evolutionary interaction between plants and insects. Cucurbitacins (cucs), allomones that originally served to protect the plants from attack by herbivores, have become kairomones for a large group of diabroticite beetles (Chambliss, et al., *Science*, 154:1392–1393 (1966), Sharma, et al, *Environ. Entomol.*, 2:154–156 (1973), Howe, et al., *Environ. Entomol.*, 5:1043–1048 (1976), Metcalf, et al., *Proc. Natl. Acad. Sci. USA*, 77:3769–3772 (1980), Metcalf, et al., *Environ. Entomol.*, 11:921–927 (1982), Ferguson, et al., *J. Econ. Entomol.*, 76:47–51 (1983), Metcalf, *Nat. Hist. Surv.*, 33:175–198 (1985), Metcalf, *J. Chem. Ecol.*, 12:1109–1124 (1986). The adult beetles detect cucurbitacins in nanogram quantities by specific sensory receptors on the maxillary palpi and respond by arrest and compulsive feeding. These kairomones influence the behavior of a number of important crop pests including the banded cucumber beetle (BCB), *Diabrotica balteata* LeConte; the northern corn rootworm (NCR), *Diabrotica barberi* Smith & Lawrence; the southern corn rootworm (SCR), *Diabrotica undecimpunctata howardi* Barber, and its western relative, *D. u. undecimpunctata* Mannerheim; the western corn rootworm (WCR), *Diabrotica virgifera virgifera* LeConte; the striped cucumber beetle (SCB), *Acalymma vittatum*, (F.), and its western relative, *Acalymma trivittatum* (Mannerheim). This specific response by diabroticite beetles to the cucurbitacin kairomones has considerable potential for the integrated pest management of cucumber beetles and corn rootworms (Rhodes, et al., *J. Am. Soc. Hortic. Sci.*, 105:838–842 (1980); Metcalf, et al., *Cucurbit Genet. Coop. Rep.*, 4:37–38 (1981); Metcalf, et al., *Cucurbit Genet. Coop. Rep.*, 6:79–81 (1983); Metcalf, *J. Chem. Ecol.*, 12:1109–1124 (1985); and Metcalf, et al., Canadian Patent No. 1,195,922 (1985)). The latter reference disclosed the addition of dried bitter Cucurbitale fruit (as opposed to the blossoms and/or blossom volatiles) as a good source of cucurbitacins. Cucurbitacins are not volatile. Because they are not volatile, they are ineffective as long-range attractants of insects. Cucurbitacins are arrestants that act as kairomones to arrest diabroticites. "Arrested" insects initiate compulsive feeding responses. That is, they stop dead in their tracks and compulsively feed on the fruits.

The laboratory experiments described below were conducted with a colony of SCR adults and with WCR adults from a nondiapausing race obtained from the USDA, Northern Grain Insects Research Laboratory, Brookings, S. Dak. The field experiments were conducted with normal Illinois populations of SCR, NCR, WCR, and SCB found in cultivated cucurbits (Cucurbita species) and corn (*Zea mays*) grown on the University Vegetable Crops Farm, Urbana, Ill.) Cucurbita fruit for bait production was grown on the University of Illinois Vegetable Crops Farm. *C. foetidissima* roots were provided by W. P. Bemis, University of Arizona.

Dried Cucurbita $F_1$ baits were produced from the fruits of the hybrids AND×MAX and TEX×PEP (Rhodes, et al., *J. Am. Soc. Hortic. Sci.*, 105:838–842 (1980)) and from the roots of *C. foetidissima*. The fruits were split, partially air-dried, then thoroughly dried in a forced-air oven at 70° C., and ground in a Wiley mill. The completely dry fruits of AND×MAX contained 8.9% solids and those of TEX×PEP contained 9.1% slids. *C. foetidissima* roots averaged 22.7% solids (Berry, et al., *J. Agric. Food Chem.*, 26:345–346 (1978)). The proportions of the ground baits passing through a screen (2 mm) were as follows: AND×MAX, 34%; TEX× PEP, 70%; and *C. foetidissima*, 98%. Baits formulated from TEX×PEP $F_2$ fruits grown in Arizona were supplied by American Cyanamid; 44% passed through a 2-mm screen.

A noncucurbit carrier, 10-mesh corn grits (71% of which passed through a 2-mm screen), was obtained from Illinois Cereal Mills, Paris, Ill. (designated as pesticide carrier grits, 980). This carrier was impregnated with different levels of cucurbitacins by addition of varying amounts of a chloroform extract of AND×MAX fruit containing 0.12% cucurbitacins B and D (Metcalf, et al., *Proc. Natl. Acad. Sci. USA*, 77:3769–3772 (1980), Metcalf, et al., *Environ. Entomol.*, 11:921–927 (1982)). The cucurbitacin-containing areas were scraped from plates, extracted in anhydrous methanol, centrifuged, and the UV absorption at 210 nm determined by UV spectrophotometry. Content of cucurbitacins was quantified from standard curves of pure cucurbitacins B, D, E and I, and E-glycoside (Metcalf, et al., *Proc. Natl. Acad. Sci. USA*, 77:3769–3772 (1980), Metcalf, et al., *Environ. Entomol.*, 11:921–927 (1982)).

To determine which cucurbitacins were active as kairomones to diabroticite beetles, thin-layer plates of silica gel with fluorescent indicator on polyethylene terephthalate (Eastman Chromogram, Eastman Kodak, Rochester, N.Y.) were developed from the chloroform extracts of dried cucurbit baits and exposed to the feeding of 100 SCR or WCR beetles for 2–4 d (Metcalf, et al., *Proc. Natl. Acad. Sci. USA*, 77:3769–3772 (1980), Metcalf, et al., *Environ. Entomol.*, 11:921–927 (1982)). The beetles fed avidly on areas with active cucurbitacins with a sensitivity of detection of ca. 0.01 $\mu$g.

The various dried, ground, and insecticide-treated baits were given preliminary field evaluation by placing uniform amounts in petri-dish halves (150-mm diameter) that were placed at random on the ground in cucurbit and corn rows heavily infested ith SCR, WCR, and SCB adults. Ten dishes were used for each treatment; the maximum dosage of dried baits used was 300 mg per dish, equivalent to 17 kg/ha. Mortality counts of adult beetles in the dishes were made after 20–40 h.

Evaluations of the various bait formulations were also made by broadcast applications to 0.04-ha plots of sweet corn. Weighed samples of the baits were broadcast over the tops of the corn plants so that a portion of the bait was retained on leaves and silks. Before treatment, the total number of rootworm beetles on the corn plants in each of the plots was estimated by counting the number on each of 50 plants and extrapolating the count to the entire plot (precount). Twenty-four hours after treatment, dead rootworm beetles on the ground were counted in each plot and expressed as a ratio of the precount (percentage killed). Three-day post-treatment counts on the corn were also determined (total number of beetles per plot) and were expressed as a ratio of the precount (percentage of reduction). Different rates of application of methomyl-impregnated bait were further evaluated in 0.02-ha sweet-corn plots in an analogous manner with 24-h posttreatment counts of dead beetles on the ground. Statistical evaluations were made with Duncan, *Biometrics*, 11:1–42 (1955) multiple range test (P=0.05).

The role of cucurbitacin kairomones as arrestants and feeding stimulants for SCR beetles was unequivocally demonstrated by the petri-dish tests summarized in Table 12.

TABLE 12

Effect of cucurbitacins (cucs), indole, and eugenol additives to corn-grit baits with 0.1% methomyl in petri-dish tests against *D. u. howardi* adults in cucurbit plots.

| Test | Bait additive(s) | No. dead and moribund beetles (x ± SD) |
|---|---|---|
| | Cucs | |
| A | None | 0a |
| | 0.0036% cucs | 7.9 ± 11.1a |
| | 0.012% cucs | 25.9 ± 18.5ab |
| | 0.036% cucs | 37.9 ± 23.3bc |
| | 0.120% cucs | 65.9 ± 28.4c |
| | Cucs, indole, or eugenol | |
| B | None | 1.2 ± 2.5a |
| | 0.1% eugenol | 0a |
| | 0.120% cucs | 22.0 ± 18.3b |
| | 0.120% cucs + 1% eugenol | 86.0 ± 50.3c |
| | 0.120% cucs + 1% indole | 9.5 ± 4.1b |

Means followed by the same letters are not significantly different (P > 0.05; Duncan's (1955) multiple range test). Test A, 3 October; test B, 24 August.

Corn-grits bait was 0.1% methomyl was ineffective, but the addition of 0.0036–0.120% cucurbitacins increased the kill proportionately. The effective dose range (Table 12) is equivalent to 67–202 g/ha of cucurbitacins. This range corresponds to previously reported field experiments in which AND×MAX and TEX×PEP baits with 0.1% methomyl were broadcast at 11–33 kg/ha or 60–240 of cucurbitacins for effective control of diabroticites (Metcalf, et al., *Cucurbit Genet. Coop. Rep.*, 4:37–38 (1981), Metcalf, et al., *Cucurbit Genet. Coop. Rep.*, 6:79–81 (1983)).

While the volatile additives eugenol and indole, are attractive to diabroticite beetles on cylindrical sticky traps (Ladd, et al., *J. Econ. Entomol.*, 76:1049–1051 (1983), Andersen, et al., *J. Chem. Ecol.*, 12:687–699 (1986), Lampman, et al., *J. Chem. Ecol.*, 13:959–975 (1987)), the combination of attractants with corn-grits bait containing 0.1% methomyl are ineffective (Table 12). However, in the presence of cucurbitacin arrestants, the incorporation of 1% eugenol improved the efficiency to kill of SCR beetles from 3- to 4-fold with the corn-grits bait (Table 12). Corresponding data from petri-dish tests with TEX×PEP bait showed that the incorporation of 1% eugenol into this bait produced a similar 4-fold increase in the kill of SCR beetles, but did not improve the efficiency of kill for WCR and SCB beetles. Indole was ineffective in improving bait performance, but the addition of 1% veratrole to the TEX×PEP bait increased the kill of SCR beetles in petri-dish tests from a mean (±SD) of 27.9±53 dead beetles for 10 dishes with 0.1% methomyl alone to 63.1±39.9 dead beetles with the bait containing veratrole.

Bait applications to evaluate various insecticides. The relative effectiveness of a variety of insecticides incorporated at 0.01–0.1% (wt/wt) in TEX×PEP dry ground bait was compared. The following insecticides were tested: bendiocarb, carbaryl, carbofuran, methomyl, oxamyl; dimethoate, malathion, isofenphos, phospholan, and mephospholan; and permethrin, cypermethrin, fenvalerate, and flucythrinate. In 1- to 3.3-m$^2$ plots of corn and cucurbits, the carbamates methomyl, carbofuran, carbaryl, and bendicarb at 0.1% were more effective than the pyrethroids permethrin, cypermethrin, fenvalerate, and flucythrinate at 0.01%. Isofenphos was the most effective of the organophosphorus insecticides evaluated in both corn and cucurbits. The overall greater effectiveness of the carbamates in these small-plot tests is attributed to their rapid kill and lack of repellent effect. The pyrethroids were somewhat repellent to the rootworm beetles.

In larger scale field evaluations in sweet corn, broadcast applications of TEX×PEP ($F_2$) bait, with both the 0.1% methomyl and 0.1% isofenphos baits produced comparable results. Apparently, both carbamates and organophosphorus insecticides are effective toxicants in cucurbitacin baits.

Optimum insecticide concentration, efficiency of application, and duration of effectiveness of baits. Although adult corn rootworm beetles frequent corn leaf sheaths, silks, and tassels during the daytime and are seldom seen on the ground, the cucurbitacin baits applied directly to the ground were surprisingly effective. Baits broadcast over the tops of corn plants were also effective at comparable rates. Both modes of bait application were highly selective. No dead predators were found after ground treatment, and dead coccinellids were observed only occasionally after broadcase treatment.

Evaluation of TEX×PEP $F_2$ bait broadcast over several corn plots at five different combinations of methomyl concentration and rates of application showed that 0.1% methomyl bait applied at 33 kg/ha was optimally effective. The application rate for methomyl along was 33.6 g/ha, and this rate of application is much more efficient than the conventional dosage of 1,121 g/ha of carbaryl for aircraft sprays to control adult corn rootworm beetles. An equal amount of methomyl (33.6 g/ha) in bait applied at 3.3 kg/ha was less effective because of inefficient distribution of bait particles over the treated area. Reduction of the total amount of methomyl in the bait from 112 g/ha to 11 g/ha while the amount of bait was kept constant at 11 kg/ha decreased the kill of rootworm beetles, although large numbers of dead beetles were found on the ground in the treated plot.

Application of AND×MAX bait containing 0.1% methomyl at 33 kg/ha to sweet-corn plots heavily infested with corn rootworm adults resulted in substantial reduction of adult beetles after 1 d (WCR, 98%, SCR, 56%; NCR, 100%). The lower apparent reduction of SCR beetles in this test compared with the previous was probably due to continued invasion of the small plots by SCR beetles. A reduction in the numbers of beetles per plot was also observed after 2 d, and incremental numbers of dead and moribund beetles were found on the ground after 3, 7, and 11 d. This indicates that the poison baits may have potential for killing diabroticites for substantial periods of time after a single application.

The foregoing results demonstrate some of the possibilities for regulating insect behavior by incorporation of plant kairomones into toxic baits. Cucurbitacins from dried bitter squash fruits or roots were very effective in arresting the several species of rootworm beetles and in causing them to feed on baits poisoned with a variety of insecticides. With rapidly acting insecticides such as methomyl, there was little or no survival from exposure to the baits.

The diabroticites are susceptible to a wide variety of organophosphorus, carbamate, and pyrethroid insecticides that could be incorporated into bitter cucurbita baits (Chio, et al., *J. Econ. Entomol.*, 71:289–393 (1978)). Factors influencing the choice of insecticide include intrinsic beetle susceptibility, repellence of beetle feeding, solubility in water, and photostability as it affects persistence of the toxic bait under the influence of sunlight and moisture. Although carbamate insecticides consistently had the lowest $LD_{50}$ values for the important pest species of rootworms (Chio, et al., *J. Econ. Entomol.*, 71:289–393 (1978)), carbamate resistance is evident especially with SCR (Chio, et al., *J. Econ. Entomol.*, 71:289–393 (1978)). Because of the very small amount of insecticide required for effective baits (Metcalf, *Nat. Hist. Surv.*, 33:175–198 (1985)), considerations of human and environmental toxicity and of the cost of insecticide are less critical than for conventional spray treatments.

The cucurbitacins were effective arrestants and feeding stimulants in such poisoned baits when broadcast at rates of 40–240 g/ha. The cucurbitacins seemed about equally effective as kairomones whether present as naturally occurring substances in dried cucurbita fruits or when extracted and impregnated in pelleted corn grits. Volatile attractants such as eugenol or veratrole improved the effectiveness of the cucurbitacin-containing baits for SCR by attracting the beetles from a distance. Such artificial kairomone baits seem to have potential for practical control of adult diabroticite beetles.

EXAMPLE 5

Cucurbita Blossom Aroma and Diabrotica Rootworm Beetle Attraction

As described inter alia, recent research has shown that many diabroticite species found on cucurbits including the striped cucumber beetle (SCB) *Acalymma vittata*, the spotted cucumber beetle (SCR) *D. undecimpunctata howardi*, the western corn rootworm (WCR) *D. virgifera virgifera*, and the northern corn rootworm (NCR) *D. barberi*, are attracted to olfactory cucs. The preponderance of previously described attractants are phenylpropanoids or closely related compounds e.g., eugenol, estragole, and 4-methoxycinnamaldehyde (Lampman, R. L., and Metcalf, R. L., *J. Econ. Entomol.*, 80:1137–1142 (1987); Lampman, R. L., Metcalf, R. L., and Andersen, J. F., *J. Chem. Ecol.*, 13:959–975 (1987)).

The attraction of Diabrotica beetles to the odors of Cucurbita blossoms was examined independent of visual and contact cucs, such as color, size, shape, and cucurbitacin content. Thirty grams of blossoms from cv. Dickinson Field (*C. moschata*) and cv. Blue Hubbard (*C. maxima*) were placed inside paper cartons, the top covered with cheesecloth (preventing contact with the blossoms), and the outside of the trap coated with sticky material. The traps were placed in a field of Blue Hubbard squash for a period of sixty minutes after which they were collected and the total number of WCR, SCR and SCB trapped were counted.

As shown in Table 13 below, the attraction of WCR and SCB beetles to the isolated Blue Hubbard blossoms demonstrates that blossom odor along plays an important role in the distribution of these rootworm beetles. The apparent lack of response from SCR adults is probably due to the extremely low number of beetles present in the field.

TABLE 13

Mean number of rootworm beetles in sticky traps baited with Cucurbita blossoms

|  | WCR | SCR | SCB |
|---|---|---|---|
| control 60 min. | 6.8 ± 7.5 | 0.5 ± 0.6 | 1.8 ± 0.5 |
| C. maxima 60 min. | 86.0 ± 30.6 | 3.0 ± 1.4 | 11.8 ± 4.5 |
| C. moschata 60 min. | 11.3 ± 6.2 | 0.5 ± 1.5 | 2.8 ± 1.5 |

Over 40 individual volatile chemicals have been isolated from *Cucurbita maxima* blossoms and circa 25 of these have been unequivocally identified (Andersen, J. F., *J. Agric. Food Chem.*, 35:60–62 (1987): Andersen, J. F. and Metcalf, R. L., *J. Chem. Ecol.*, 12:687–699 (1986)). The major odor components were evaluated as potential attractants for adult Diabrotica species using cylindrical sticky traps baited with dental cotton wicks (Metcalf, R. L., and Lampman, R. L., Paper submitted to *J. Econ. Entomol.*, (1988)) containing from 0.01 mg to 200 mg of volatile compound.

The effective attractants show a linear log-dosage response and the attractive compounds have been rated according to their limit of response (LR), i.e. the least amount of compound producing significant attraction over a 24 hour period vis-a-vis unbaited control traps as follows:

| Amount [in mgs] | Rating |
|---|---|
| 200 | 0 |
| 30–100 | +1 |
| 10–30 | +2 |
| 3–10 | +3 |
| 1–3 | +4 |

The results are based on the means of four replicate traps and were significantly different from the control traps at $P=0.01$ by Duncan's multiple range test (Nie, et al., supra). A summary of the results obtained are shown in Table 14.

TABLE 14

Summary of attraction of rootworm beetles to sticky traps baited with individual components of squash blossom volatiles

| Volatile: | Attractant Rating | | |
|---|---|---|---|
|  | NCR | SCR | WCR |
| green volatiles: | | | |
| 1-hexanol | 0 | 0 | 0 |
| 1-hexanal | 0 | 0 | 0 |
| trans-2-hexenol | 0 | +1 | +1 |
| cis-3-hexenol | 0 | 0 | +1 |
| trans-2-hexenal | 0 | 0 | 0 |
| aromatics: | | | |
| 1,4-dimethoxybenzene | 0 | 0 | 0 |
| 1,2,4-trimethoxybenzene | 0 | +1 | +1 |
| benzyl alcohol | 0 | 0 | 0 |
| benzaldehyde | 0 | 0 | 0 |
| phenylethanol | 0 | +1 | 0 |
| phenylacetaldehyde | 0 | +2 | 0 |
| p-methoxybenzyl alcohol | 0 | 0 | 0 |
| p-methoxybenzaldehyde | 0 | 0 | 0 |
| phenyl propanoids: | | | |
| indole | 0 | 0 | +4 |
| cinnamyl alcohol | +3 | +2 | +1 |
| trans-cinnamaldehyde | 0 | +4 | +3 |
| terpenoids: | | | |
| α-ionone | 0 | 0 | 0 |
| β-ionone | 0 | 0 | +4 |
| nerolidol | 0 | 0 | 0 |

As is clear from the results shown in Table 14, the majority of the *C. maxima* blossom volatiles are unattractive when tested singularly. The green volatiles, especially trans-2-hexenol and cis-3-hexenol, are marginally attractive, as are the aromatic compounds, 1,2,4-trimethoxybenzene, phenylethanol, and phenylacetaldehyde for SCR. Trans-cinnamaldehyde is highly attractive to SCR and moderately attractive to WCR, but not appreciably attractive to NCR, Trans-cinnamyl alcohol is highly attractive to NCR, although only slightly attractive to SCR and WCR. Indole is highly attractive to WCR (LR 1 mg), but not appreciably attractive to NCR and SCR. The terpenoid, β-ionone, is highly attractive to WCR (LR 3 mg), but unattractive to NCR and SCR. Its isomer α-ionone is completely unattractive to all three Diabrotica species. In contrast, the most effective volatile attractants yet identified for the respective species and their LR values are eugenol for NCR (LR 10 mg), estragole for WCR (LR 3 mg), and 4-methoxycinnamaldehyde for WCR (LR 0.03 mg) Metcalf, R. L., and Lampman, R. L., Paper submitted to *J. Econ. Entomol.*, (1988).

EXAMPLE 6

Evaluation of Compounds Including Phenylethanol Analogues as Attractants

Test chemicals (purchased from Aldrich Chemical Co.; Milwaukee, Wis.) were applied by capillary micropipettes to cotton dental wicks that were attached to tops of 1.0 liter cylindrical paper cartons covered with TangleTrap™, Grand Rapids, Mich. The trapping techniques used were as previously described in Example 1. Unless otherwise indicated, all treatments were made at a dosage of 100 mg or 100 μL of attractant per trap. Control traps had untreated wicks. Four replicates of treated and untreated traps were positioned randomly 10 meters apart on top of 1 m high posts along the edges of 25–50 ha. fields of hybrid corn (*Zea mays*), infested with adult NCR, SCR, and WCR beetles. Several experiments detailed in the Tables were made in a 0.4 ha plot of sweet corn (Illini X-tra Sweet).

Attraction of Diabrotica species adults of the sticky traps was measured by the mean number of beetles caught after 1 day (ca. 24 hours) exposure. The significance of the treatments was determined by analysis of variance and the individual means were separated by Duncan's multiple range test (Statistical Package for the Social Sciences, Nie, et al., 2nd. ed. McGraw-Hill, New York (1975). The data was logarithmically transformed for statistical analysis. Means and standard deviations are presented for the untransformed data. Significance levels were set at P=0.05 for all statistical analyses.

The response of NCR and WCR adults in corn to sticky traps baited with 4-methoxyphenylethanol, 4-methylphenylethanol, 4-chlorophenylethanol, 4-fluorophenylethanol, 4-nitrophenylethanol, p-aminophenylethanol, control (untreated), phenyl ethanol, and 4-methoxycinnamaldehyde is shown in Table 15, below.

This experiment demonstrates that 4-methoxyphenylethanol is much more attractive to NCR than phenylethanol and that attraction is by far the greatest with para-substitution with a methoxy group. Despite the presence in this field of large numbers of Western corn rootworm adults, as evidenced by the high catch obtained using 4-methoxycinnamaldehyde (a WCR attractant), WCR were not attracted by any of the phenylethanols.

TABLE 15

Mean number of northern corn rootworm (NCR) and western corn rootworm (WCR) per trap (± standard deviation); four replicates; 24 hour evaluation.

| Treatment | NCR | WCR |
|---|---|---|
| 4-methoxyphenylethanol | 187.7 ± 62.5d* | 5.7 ± 2.8a |
| 4-methylphenylethanol | 89.2 ± 7.8c | 12.2 ± 5.6a |
| 4-chlorophenylethanol | 30.0 ± 7.4b | 13.7 ± 3.9a |
| 4-fluorophenylethanol | 38.0 ± 6.2b | 14.0 ± 12.3a |
| 4-nitrophenylethanol | 7.7 ± 2.7a | 7.9 ± 5.1a |
| 4-aminophenylethanol | 10.5 ± 2.1a | 8.5 ± 3.4a |
| control (untreated) | 7.5 ± 3.3a | 7.2 ± 1.5a |
| phenyl ethanol | 50.0 ± 20.9b | 18.7 ± 10.2a |
| 4-methoxycinnamaldehyde | 6.4 ± 4.9a | 567.5 ± 111.6b |

*means in the same column followed by the same letter are not significantly different (p = 0.05) by Duncan's multiple range test.

The results shown in Table 16, below, demonstrate that the para-isomer of methoxyphenylethanol is much more attractive to NCR than the ortho and meta-isomers, and that para-methoxyphenylethanol is a more effective attractant than cinnamyl alcohol.

TABLE 16

Mean number of Northern corn rootworm (NCR) and Western corn rootworm (WCR) per trap (± standard deviation); four replicates, 24 hour evaluation.

| Treatment | NCR | WCR |
|---|---|---|
| 4-methoxyphenylethanol | 60.3 ± 26.8b* | 3.5 ± 2.1a |
| 3-methoxyphenylethanol | 7.2 ± 3.4a | 3.7 ± 2.1a |
| 2-methoxyphenylethanol | 13.5 ± 9.3a | 6.0 ± 5.1a |
| cinnamyl alcohol | 50.7 ± 50.9b | 4.0 ± 1.6a |
| control (untreated) | 4.7 ± 1.9a | 2.2 ± 1.9 |

*means in the same column followed by the same letter are not significantly different (p = 0.05) by Duncan's multiple range test.

The results shown in Table 17 demonstrate that 4-methoxyphenyl ethanol is the most effective and specific NCR attractant evaluated. Increase in side-chain length and removal of 4-methoxy group decreased activity.

TABLE 17

Mean number of Northern corn rootworm (NCR) and Western corn rootworm (WCR) per trap (± standard deviation); four replicates, 24 hour evaluation.

| Treatment | NCR | WCW |
|---|---|---|
| phenylethanol | 12.2 ± 5.5b* | 9.2 ± 9.2a |
| phenylpropanol | 36.2 ± 12.2c | 4.0 ± 2.9a |
| 4-methoxyphenylethanol | 56.7 ± 7.5c | 6.0 ± 4.2a |
| 4-methoxyphenylpropanol | 15.5 ± 6.2b | 3.2 ± 2.2a |
| cinnamaldehyde | 15.5 ± 3.8b | 56.0 ± 34.6b |
| 4-methoxycinnamaldehyde | 2.5 ± 1.9a | 360.2 ± 181.3c |
| control (untreated) | 3.5 ± 1.0a | 4.0 ± 1.6a |

*means in the same column followed by the same letter are not significantly different (p = 0.05) by Duncan's multiple range test.

The results shown in Table 18, below demonstrate that 4-methoxyphenylethanol is much more attractive to NCR than cinnamyl alcohol and further demonstrate that levels as low as 0.1 mg of 4-methoxyphenylethanol are attractive to NCR.

TABLE 18

Mean number of Northern corn rootworm (NCR) per trap (± standard deviation); four replicates, 24 hour evaluation

| Treatment | NCR |
|---|---|
| cinnamyl alcohol | |
| 30 mg | 15.2 ± 4.2c* |
| 10 mg | 8.5 ± 2.1bc |
| 3 mg | 4.0 ± 0.8ab |
| 1 mg | 3.5 ± 2.4a |
| control (untreated) | 2.2 ± 1.2a |
| 4-methoxyphenyl ethanol | |
| 3 mg | 72.0 ± 10.8d |
| 1 mg | 41.0 ± 23.4c |
| 0.3 mg | 32.7 ± 9.4c |
| 0.1 mg | 16.2 ± 1.2b |
| control (untreated) | 4.5 ± 0.6a |

*means in the same column followed by the same letter are not significantly different (p = 0.05) by Duncan's multiple range test.

A comparative experiment was undertaken to compare the effective time duration of attraction for a single 100 mg dosage of attractant. The attractants selected were eugenol, cinnamyl alcohol, phenyl propanol, phenylethyl amine, and 4-methoxyphenylethanol. Eugenol and cinnamyl alcohol were chosen for this comparison study because these two compounds have been shown to be effective attractants for NCR. The results are shown in Table 19, below.

TABLE 19

Effective time duration of attraction from single 100 mg dosage of attractant on cotton wicks on cylindrical sticky traps; treated cotton wicks are transferred to a new cylindrical sticky trap at the indicated interval after original treatment. Mean number (control subtracted) of Northern corn rootworm (NCR) per trap; four replicates.

| | Treatment | | | | |
|---|---|---|---|---|---|
| Days | eugenol | cinnamyl alcohol | phenyl propanol | phenyl ethyl amine | 4-methoxy phenylethanol |
| 1 | 88.2 | 52.0 | 76.5 | 85.9 | 134.5 |
| 2 | 67.3 | 65.3 | 115.3 | 125.3 | 231.8 |
| 3 | 14.3 | 17.3 | 38.8 | 39.4 | 93.1 |
| 4 | 18.0 | 19.5 | 25.0 | 27.5 | 51.5 |
| 5 | 20.7 | 17.7 | 41.8 | 155.4 | 128.9 |
| 6 | 29.9 | 7.7 | 10.5 | 44.2 | 49.2 |
| 7 | 30.2 | 10.4 | 10.7 | 38.4 | 76.7 |
| 8 | 35.5 | 11.0 | 29.5 | 17.5 | 99.0 |
| 11 | 10.0 | 9.8 | 4.5 | 3.8 | 64.8 |

The results of this comparative study demonstrate that all compounds tested are effective attractants for NCR. However, 4-methoxyphenylethanol remains a highly effective attractant for the greatest length of time.

Another comparative study was undertaken to compare the effectiveness of various amine derivatives including: benzylamine, phenylethylamine, phenylpropylamine, phenylbutylamine, 4-methoxyphenyl-ethylamine and cinnamyl alcohol. These compounds were chosen because they are structural analogues of the phenyl alkanols incorporating the nitrogen atom with an unshared pair of electrons, analogous to those in the phenyl alkanols.

TABLE 20

Mean number of Northern corn rootworm (NCR) per trap (± standard deviation); four replicates; 24 hour evaluation.

| Treatment | NCR |
|---|---|
| benzylamine | 57.5 ± 29.6b* |
| phenylethylamine | 206.7 ± 32.3d |
| phenylpropylamine | 131.5 ± 16.5c |
| phenylbutylamine | 12.2 ± 6.1a |

TABLE 20-continued

Mean number of Northern corn rootworm (NCR) per trap (± standard deviation); four replicates; 24 hour evaluation.

| Treatment | NCR |
|---|---|
| 4-methoxyphenylethylamine | 24.2 ± 15.4a |
| cinnamyl alcohol | 127.0 ± 24.2b |
| control (untreated) | 10.5 ± 7.9a |

*means in the same column followed by the same letter are not significantly different ($p = 0.05$) by Duncan's multiple range test.

This experiment demonstrates that phenylethylamine and phenylpropylamine are most effective as attractants for NCR.

The foregoing illustrative examples relate to lures for attracting the adult form of Diabrotica species and to the use of these lures individually or in mixtures, or in combination with insecticides and/or compulsive feeding stimulants. While the present invention has been described in terms of specific methods and compositions, it is understood that variations and modifications will occur to those skilled in the art upon consideration of the present invention.

Accordingly it is intended in the appended claims to cover all such equivalent variations which come within the scope of the invention as claimed.

What is claimed is:

1. In a method for attracting northern corn rootworm, the improvement comprising the step of employing an effective amount of a compound selected from the group consisting of:

4-methylphenylethanol, 4-methoxyphenylethanol, 3-methoxyphenylethanol, 2-methoxyphenylethanol 4-chlorophenylethanol, 4-fluorophenylethanol, 4-methoxyphenylpropanol, phenyl propanol, phenylethylamine; and phenylpropylamine.

2. The method according to claim 1 further comprising: applying said compound to a lure attached to a trap.

3. The method according to claim 1 further comprising: applying said compound to an area inhabited by said northern corn rootworm.

* * * * *